United States Patent [19]
Curtiss

[11] Patent Number: 5,126,240
[45] Date of Patent: Jun. 30, 1992

[54] HYBRIDOMAS AND MONOCLONAL PARATOPIC MOLECULES TO APOLIPOPROTEIN A-I

[76] Inventor: Linda K. Curtiss, 8926 Flanders Dr., San Diego, Calif. 92126

[21] Appl. No.: 913,061

[22] Filed: Sep. 29, 1986

[51] Int. Cl.⁵ .................. G01N 33/53; G01N 33/543; C12N 5/00
[52] U.S. Cl. .................. 435/7.94; 530/326; 530/327; 530/806; 530/388.25; 435/240.27; 435/810; 435/7.93; 435/7.1; 436/548; 436/518; 436/808; 935/96; 935/110
[58] Field of Search .............. 530/326, 327, 806, 387; 435/240.27, 810, 7, 548, 518, 808; 935/96, 110

[56] References Cited
PUBLICATIONS

L. K. Curtiss, Immunochemical Heterogeneity of Human Plasma High Density Lipoproteins, The Journal of Biological Chemistry, vol. 260, No. 5, Mar. 10, 1985, pp. 2982–2993.
Curtiss et al., J. Biol. Chem., 263:13779–13785 (1988).

Primary Examiner—Christine Nucker
Assistant Examiner—Laurie A. Scheiner

[57] ABSTRACT

Hybridomas and their secreted paratopic molecules that immunoreact with apolipoprotein A-I are disclosed, as are assay methods for determining the presence and amount of apo A-I, and diagnostic systems useful in performing those determinations. Monoclonal paratopic molecules secreted by hybridomas having ATCC accession numbers HB 9200, HB 9201, HB 9202, HB 9203 and HB 9204 are utilized.

25 Claims, 2 Drawing Sheets

HYBRIDOMAS AND MONOCLONAL PARATOPIC MOLECULES TO APOLIPOPROTEIN A-I

DESCRIPTION

1. Technical Field

The present invention relates to apolipoprotein A-I, and particularly to hybridomas and monoclonal paratopic molecules useful for assaying apolipoprotein A-I in a liquid sample, as well as a diagnostic method and system for carrying out such an assay.

2. Background of the Invention

A. Atherosclerosis and Lipoproteins

Atherosclerosis is the disease in which cholesterol and other lipids, accumulating on the walls of arteries, form bulky plaques that inhibit the flow of blood and may lead to the formation of a clot, which can obstruct an artery and cause occlusive thrombotic or embolic disease such as a heart attack or stroke. Up to 50 percent of all deaths in the United States are caused by atherosclerosis and its secondary complications.

Human atherosclerosis is defined as the accumulation of selected lipids, including cholesterol, and cells in the walls of arteries and with time produces occlusive lesions. Although the etiology of atherosclerosis is multifactorial, a large body of clinical, pathologic, genetic and experimental evidence suggests that abnormalities of lipoprotein metabolism can contribute to the development of atherosclerosis. These lipids are carried in the blood stream as lipid-protein complexes called lipoproteins.

Atherosclerosis, and particularly that form known as coronary artery disease (CAD), is a major health problem. Atherosclerosis and its related vascular diseases accounted for 983,000 deaths in 1983; and CAD alone accounts for more deaths annually than all forms of cancer combined. In the United States, more than 1 million heart attacks occur each year and more than five hundred thousand people die as a result of this disease. In direct health care costs, CAD costs the United States more than $60 billion a year. This enormous toll has focused attention on ways to identify particular populations at risk for CAD so that the disease can be controlled with diet, behavioral modification (exercise), and specific therapeutic agents.

Because of the major implication of cholesterol in CAD, that molecule and its associated plasma proteins have been extensively studied. Four major classes of cholesterol-associated plasma lipoprotein particles have been defined, and have their origin in the intestine or liver. These particles are involved in the transport of the neutral lipids including cholesterol and triglycerides. All classes of plasma lipoproteins have apolipoproteins associated with the lipid-protein complex; and the apolipoproteins play requisite roles in the function of these lipoproteins.

The first class is the chylomicrons. They are the largest of the lipoproteins and are rich in triglycerides. The site of origin of the chylomicrons is the intestine.

Whereas apolipoproteins are a quantitatively minor proportion of the mass of chylomicrons, apolipoproteins A-I, A-II and A-IV are reportedly significantly associated with chylomicrons, and intestinal synthesis of these A apolipoproteins has been found. Chylomicrons also contain apolipoprotein B-48. Much of the chylomicron complement of A apolipoproteins is lost, and C and E apolipoproteins are acquired when chylomicrons are exposed to plasma or high density lipoprotein (HDL) in vitro. Intestinal production of the A apolipoproteins (apo A) may be regulated by factors other than fat absorption and chylomicron formation.

The next class of lipoproteins is the very low density lipoproteins, VLDL. The VLDL particle is involved in triglyceride metabolism and transport of these lipids from the liver. The apolipoproteins apo B-100 and apo E are the major constituents of the VLDL particle.

The third lipoprotein is called low density lipoprotein (LDL), and is a specific product of the catabolism of VLDL. The predominant apolipoprotein in the LDL particle is apolipoprotein B-100, or apo B-100.

The results of the now classic Framingham study (1971) showed a clear correlation between risk for CAD and serum cholesterol levels. This study also demonstrated that elevated levels of low density lipoprotein (LDL) cholesterol are associated with increased risk of CAD. Recently, a study conducted by the Lipid Research Clinics Coronary Primary Prevention Trial (1984) has demonstrated that plasma levels of cholesterol and LDL cholesterol can be reduced by a combined regime of diet and drugs, and that this reduction of plasma cholesterol results in reduction of the incidence of CAD mortality.

LDL is the major cholesterol-carrying lipoprotein in plasma. LDL is a large spherical particle whose oily core is composed of about 1500 molecules of cholesterol, each attached by an ester linkage to a long chain fatty acid. This core of cholesteryl esters is enclosed by a layer of phospholipid, unesterified cholesterol molecules and a single molecule of apolipoproein B-100. The phospholipids are arrayed so that the hydrophilic heads are on the outside, allowing the LDL to be in hydrated suspension in the blood or extracellular fluids.

The cholesterol is delivered to cells on LDL via a specific LDL receptor, and is liberated from the LDL particles in lysosomes where it can control the cell's cholesterol metabolism. An accumulation of intracellular cholesterol modulates three processes.

First, it reduces the cell's ability to make its own cholesterol by turning off the synthesis of an enzyme, HMG CoA reductase, that catalyzes a step in cholesterol's biosynthetic pathway. Suppression of the enzyme leaves the cell dependent on external cholesterol derived from the receptor-mediated uptake of LDL.

Second, the incoming LDL-derived cholesterol promotes the storage of cholesterol in the cell by activating an enzyme denominated lipoprotein acyltransferase. That enzyme esterifies fatty acids to excess cholesterol molecules, making cholesteryl esters that are deposited in storage droplets.

Third, and most significant, the accumulation of cholesterol within the cell drives a feedback mechanism that makes the cell stop synthesizing new LDL receptors. Cells thereby adjust their complement of external receptors so that enough cholesterol is brought into the cells to meet the cells' varying demands but not enough to overload them. For example, fibroblasts that are actively dividing, so that new membrane material is needed, maintain a maximum complement of LDL receptors of about 40,000 per cell. In cells that are not growing, the incoming cholesterol begins to accumulate, the feedback system reduces receptor manufacture and the complement of receptors is reduced as much as tenfold.

On the other hand, it has been shown that another circulating lipoprotein, high density lipoprotein (HDL)

particle is implicated in a state of elevated cholesterol associated with lowered risk of atherosclerosis. Apolipoprotein A-I is a structural protein and ligand of the HDL particle. The amount of HDL provides an inverse correlation with the predicted incidence of atherosclerosis.

High density lipoprotein (HDL) contains two major apolipoproteins, apolipoprotein A-I (apo A-I) and apolipoprotein A-II (apo A-II). Apo A-I is the major protein component of all primate HDL. All HDL particles contain apo A-I, and therefore immunoquantification of HDL has usually involved the quantitation of apo A-I. About 80 percent of HDL particles also contain apo A-II, but HDL particles containing only apo A-II have not been described.

One function of apo A-I is the activation of the plasma enzyme, lecithin-cholesterol acyltransferase (LCAT). This enzyme is required for the esterification of free cholesterol on HDL for transport to the liver. In the absence of apo A-I, cholesterol in the blood is not esterified and thus cholesterol is not cleared from the blood. The specific role in HDL metabolism served by apo A-II has not been defined.

Many studies have shown that elevated HDL levels correlate with a reduced incidence of CAD. Some authors have speculated that HDL removes cholesterol from peripheral sites, such as the arterial wall, therefore attributing anti-atherogenic properties to HDL. Higher concentrations of HDL cholesterol are correlated with relatively normal lipid metabolism and a lower incidence of and/or a decreased severity of cardiovascular disease, whereas elevated levels of LDL cholesterol are associated with abnormal lipid metabolism and an increased risk of CAD. For the proper management of patients with hyperlipidemia (excess lipids in the blood) and those patients at special risk for CAD, it is desirable to frequently determine levels of LDL and HDL cholesterol. To date, assays of HDL cholesterol have been cumbersome and inaccurate in determining blood levels of HDL.

B. Lipoprotein Structure and Function

It is important to understand that cholesterol does not exist free in plasma but is transported to tissue sites in the body by lipoproteins. Cholesterol can be obtained from directed cellular synthesis or by diet. However, cholesterol can be removed from the host only by the liver, where it is converted to bile acids and excreted.

Chylomicrons carry cholesterol and triglycerides to the liver for subsequent processing, whereas, LDL delivers cholesterol to extrahepatic tissues, including the coronary arteries. Hence, the lipoprotein, LDL/apo B, is involved in the deposition of "bad" cholesterol in peripheral tissue. Conversely, the lipoprotein HDL/apo A, removes "good" cholesterol from the tissues and returns cholesterol to the liver for excretion.

Historically, many systems have been developed to isolate and to characterize lipoproteins. These techniques are usually based upon the physicochemical properties of the lipoprotein particles. The two most frequently used techniques are ultracentrifugation and electrophoresis.

Differential density gradient ultracentrifugation takes advantage of the fact that the lipoproteins are lighter or less dense, than other plasma proteins, and it is relatively easy, though time-consuming and cumbersome, to separate the chylomicrons (the lightest lipoproteins), VLDL, LDL and HDL from each other. Electrophoretic techniques have been useful for the classification of patients with hyperlipidemias. However, these techniques are not easily carried out in an ordinary clinical laboratory.

One can also see that the simple quantitation of blood cholesterol or triglycerides does not provide the physician with the information about which lipoproteins are carrying these lipids and their quantitation.

C. The Plasma Lipoproteins

Four major classes of plasma lipoproteins; i.e., chylomicrons, VLDL, LDL and HDL, have been defined, and subclasses within these undoubtedly exist. All lipoproteins have their origin in the intestine or liver, or both, and appear to have a pseudomicellar structure. Neutral lipids, and particularly, cholesterol esters and triglycerides, are maintained in the core of the lipoproteins in a soluble and stable form through interactions with the surface polar constituents, apolipoproteins and phospholipids.

Unesterified cholesterol is also present in these complexes. Its polarity lies between that of the neutral lipids (cholesteryl esters and triglycerides) and that of the more polar apolipoproteins and phospholipids, and is found both in the core and on the surface.

An outer surface consisting of apolipoproteins, unesterified cholesterol, and phospholipids surrounds a water-insoluble core of cholesteryl esters and triglycerides, protecting the apolar lipids from the aqueous environment. This general structural concept has been supported by low-angle x-ray scattering studies and by other physical methods in which a variety of probes have been used to explore the structure of the lipoproteins. An important function of the plasma lipoproteins is thus the solubilization and transport of the neutral plasma lipids.

D. The Apolipoproteins

Apolipoproteins are the lipid-free protein components of the plasma lipoproteins obtained by treating isolated intact lipoproteins with organic solvents, detergents, or chaotropic agents. Not all proteins captured with lipoproteins necessarily have a role in lipid transport. A pertinent example is the recent recognition that the serum amyloid A proteins, acute phase reactants, are transported in plasma bound to HDL. These low molecular weight proteins may comprise up to 30 percent of apo-HDL in inflammatory states, but it is doubtful that they have specific lipid transport roles.

The apolipoprotein A-I (apo A-I) present in HDL particles is the protein of interest in the present invention. Apo A-I is discussed below.

Apo A-I is the major protein component of all primate HDL, is present in all HDL particles and there are multiple, e.g. about 7–8, apo A-I molecules per HDL particle. It has been reported to be present in relatively minor amounts in chylomicrons, VLDL and LDL as well as constituting about 60–80 percent of the protein of HDL.

Apo A-I consists of a single chain of 243 to 245 residues; does not contain cystine, cysteine, leucine, or carbohydrate; and exists in several isoforms. Apo A-I has an alpha helical content of about 55 percent in the lipid-free state, which increases to about 75 percent upon binding phospholipid. Repeating cycles of 11 helical residues have been identified in this apolipoprotein. It has been suggested that these units represent a single ancestral chain which, by gene duplication, has generated a 22-residue repeat unit. These units have close sequence homology and are believed to represent the lipid-binding regions of the protein.

As noted previously, apo A-I is potent activator of LCAT, a plasma enzyme that catalyzes the conversion of cholesterol and phosphatidylcholine to cholesteryl ester and lysophosphatidylcholine, respectively. Specific lipid-binding regions of apo A-I have been found to activate LCAT, and this activity has been associated with the property of lipid binding. As already noted, liver and intestine synthesize apo A-I, but their relative contributions to the total plasma content and the factors modulating apo A-I production are not well defined.

Typically, more than about 90 percent of plasma apo A-I is associated with HDL, less than about 1 percent with VLDL and LDL, and about 10 percent or less is associated with the lipoprotein-free fraction of plasma. The amounts of apo A-I in each particle type differs with those who report the data and appears to be a functon of the techniques used in separation of the particles.

Measurement of the major protein constituent of HDL, apo A-I, is clinically important. The results of a number of studies have demonstrated that apo A-I levels are decreased in subjects with CAD. This observation stresses the protective role of plasma apo A-I in this patient group.

The results of several studies suggest that by measuring the apo A-I level accurately, it may be possible to predict an individual's prognosis for abnormal lipid metabolism, atherosclerosis, and specifically for CAD. However, the amount of apo A-I alone has not been capable of utilization as a marker for abnormal lipid metabolism if only because of its difficulty in accuracy and precision of measurement. Thus, whereas relatively high apo A-I levels tend to correlate with normal lipid metabolism and relatively low levels with abnormal lipid metabolism and CAD, a clear line of demarcation between normal persons and those with known CAD has not been reported.

As noted before, apo A-I has been found extremely difficult to accurately and precisely quantify in a clinically useful immunoassay system such as a radioimmunoassay (RIA), an enzyme-linked immunoassay (ELISA), an electroimmunoassay (EIA), a radialimmunodiffusion (RID) or by immunonephelometry (INA). See, for example, Table 1 of Steinberg et al. (1983) *Clin. Chem.* 29/3:415–426 for the variance in values reported using various techniques.

One of the reasons alleged for these analytical difficulties is that the apolipoprotein A-I molecule is present in plasma and serum as part of a large, biochemically heterogeneous particle, within which some of the molecules antigenic sites (epitopes) are concealed and masked. As a consequence, several workers have utilized unmasking treatments for their samples so that the normally concealed epitopes are unmasked, and available for immunoreaction.

Steinberg et al. (1983) *Clin. Chem.* 29:15–426 also discuss unmasking by treatment of a blood sample such as plasma or serum with denaturing agents such as urea, tetramethyl urea and guanidine, surfactants such as sodium dodecyl sulfate and polyoxyethylene (20) sorbitan monolaurate (Tween 20), heating as at 52 degrees C. for 3 hours and at 37 degrees C. for 2 hours, and delipidating organic solvents such as mixtures of ethanol and diethyl ether, methanol and diethy ether, chloroform and methanol, and the like. Additional specific unmasking treatments can be found in the work reported by Maciejko et al. (1982) *Clin. Chem.* 28:199–204 (surfactant); Koren et al. (1985) *Clin. Chim. Acta* 147:85–95 (organic solvent); and Bury et al. (1985) *Clin. Chem.* 31:247–251 (37° C., 2 hours).

Some of the above workers and others have also utilized polyclonal antibody preparations to help avoid the apparent heterogenicity of apo A-I as it exists in plasma and serum. Maciejko et al. (1982) *Clin. Chem.* 28:199–204; Koren et al. (1985) *Clin. Chim. Acta* 147:85–95; Bury et al. (1985) *Clin. Chem.* 31:247–251; and Fesmire et al. (1984) *Clin. Chem.* 30:712–716. Of course, the use of polyclonal antibodies in a clinically useful quantitative immunoassay carries with it the detriment of differences in antibody activity attendant in use of sera from several animals, and also differences in immunospecificity from different batches of serum.

Still further, Kottke et al. (1986) *Mayo Clin. Proc.* 61:313–320, measured the levels of apolipoproteins A-I, A-II and B, HDL cholesterol, triglycerides and age as variables in males, and found that the use of all six of those variables were required to accurately discriminate CAD patients from asymptomatic controls. Those workers utilized radioimmunoassays for their determinations.

Polyclonal antibodies, an antibody-sample maintenance time of 16 hours, and an unmasking, detergent treatment were reportedly utilized for the RIA measurement of apo A-I values by Kottke et al. A monoclonal antibody was reportedly utilized for the RIA measurement of apo B. Kottke et al. reported mean apo A-I values for normals and CAD patients that did not overlap within one standard deviation.

On the other hand, aside from the monoclonal paratopic molecules utilized herein, no other workers have described monoclonal antibodies that immunoreact substantially equally with HDL particles and apo A-I, as well as immunoreact with substantially all of the apo A-I present in a sample. Thus, Curtiss et al. (1985) *J. Biol. Chem.* 200:2982–2998 reported one monoclonal antibody designated A-I-7 that immunoreacted about equally with apo A-I and HDL, but was capable of immunoprecipitating only about 60 percent of radiolabeled apo A-I or HDL known to be present in the samples assayed.

3. Monoclonal Paratopic Molecules as Reagents for Apo A-I

The use of monoclonal antibodies or their antibody combining site portions; i.e., (paratopic molecules, as reagents for assaying for the presence of apo A-I in human blood samples is attractive because once obtained, such reagents can be produced in relatively large amounts with consistent quality, and thus avoid the inconsistency problem associated with polyclonal antibodies. However, there are a number of factors that militate against the use of a particular monoclonal paratopic molecule as a component in such assay systems.

Using a monoclonal antibody as exemplary of a monoclonal paratopic molecule, the art teaches that a monoclonal antibody can be too immunospecific to be useful because of the antigenic heterogeneity of its target antigen. For example, the specificity of conventional polyclonal antibody-containing antisera depends on a consensus of hundreds of thousands of different antibodies that bind to antigenic determinants covering most or all of an antigenic protein, as has been found useful in apo A-I assays. As a result, small changes in the structure of the antigen due to genetic polymorphism, heterogeneity of glycosylation or slight denaturation or other reaction will usually have little effect on polyclonal antibody binding. Similarly, a larger or smaller subset of antibodies from polyclonal antisera will usually bind antigens that have been modified or denatured.

In contrast, monoclonal antibodies usually bind to one antigenic determinant (epitope) on the antigen molecule. If, for any reason, that determinant is altered, the antibody may or may not continue to bind. Whether this is a problem or an advantage depends on the individual circumstances. If, as in the present case, the monoclonal antibody is to be used in a diagnostic assay for an apolipoprotein, a minor antigenic variation in that protein could cause gross errors.

Second, because of their unique specificity, the successful use of a monoclonal antibody (Mab) is often dependent on its affinity for the target antigen. For instance, whereas a Mab may have sufficient affinity to be useful in binding liquid and solid phase antigen whereas the Mab is itself in the liquid phase, that same antibody may not be useful as a solid phase-bound antibody that is useful in binding to and retaining the antigen from solution.

The above problems are generic to the use of monoclonal antibodies. Those skilled in the art have therefore recognized that it is essential to test and characterize monoclonal antibodies in any assay system in which they are to be used. See Goding, James W., *Monoclonal Antibodies: "Principles and Practice"*, Academic Press, New York (1983), pages 40–46.

BRIEF SUMMARY OF THE INVENTION

The present invention contemplates hybridomas and the monoclonal paratopic molecules secreted by those hybridomas that immunologically react with apolipoprotein A-I as well as methods for assaying for the presence of apolipoprotein A-I or HDL in a liquid sample and a diagnostic system typically in kit form that is useful in carrying out the assay methods, particularly on a liquid blood sample.

Thus, one aspect of the invention contemplates a hybridoma that is selected from the group of hybridomas having the ATCC accession numbers HB 9200, HB 9201, HB 9202, HB 9203, and HB 9204. The invention further contemplates the monoclonal paratopic molecules that are secreted by each of those hybridomas and react with apolipoprotein A-I. Those monoclonal paratopic molecules are preferably whole monoclonal antibodies.

A further aspect of the invention is a method for assaying for the presence of apolipoprotein A-I in a liquid sample. That method comprises the steps of admixing a liquid sample to be assayed with an effective amount of one of the before-mentioned five monoclonal paratopic molecules to form an admixture. That admixture is maintained under biological assay conditions for a predetermined period of time sufficient for the paratopic molecules to immunoreact with apolipoprotein A-I present in the sample and form an immunoreactant. The presence of the immunoreactant is thereafter determined, thereby determining the presence of apolipoprotein A-I in the original sample. In this embodiment of the invention, the paratopic molecules preferably contain an operatively-linked radioactive element as an indicating means, and the presence of apolipoprotein A-I in the original sample is determined by separating the immunoreactant from the remainder of the admixture and assaying for emitted radiation of the separated immunoreactant.

In another embodiment of the assay method, the first-named monoclonal paratopic molecules are bound to a solid matrix to form a solid support prior to formation of the admixture. The non-specific protein binding sites of that solid support are blocked. The immunoreactant that is formed after admixture of the liquid sample is bound to the solid support as a solid phase-bound immunoreactant. In this embodiment, it is preferred that the presence of a solid phase-bound immunoreactant be determined by the use of second monoclonal paratopic molecules.

Here, liquid phase second monoclonal paratopic molecules are admixed with the above, first-named admixture to form a second admixture. Those second paratopic molecules immunoreact with apolipoprotein A-I and are selected from the before-mentioned monoclonal paratopic molecules, but are not those molecules utilized in the first-named admixture, nor is the immunoreaction of those second monoclonal paratopic molecules substantially blocked or inhibited by the immunoreaction of the first-named paratopic molecules. Those second paratopic molecules are operatively linked to an indicating means that is preferably an enzyme.

The second admixture so formed is maintained under biological assay conditions for a predetermined period of time sufficient for the second indicating means-linked paratopic molecules to immuoreact with apolipoprotein A-I present in the admixture. The solid and liquid phases formed after the admixture of both paratopic molecules, and the formation of immunoreactants, are separated, and the presence of indicating means-linked apolipoprotein A-I in the separated solid phase is determined, thereby determining the presence of apolipoprotein A-I in the sample.

The monoclonal paratopic molecules of the present invention are also useful in quantitative assays for the amount of apolipoprotein A-I in a liquid sample, particularly in a liquid blood sample such as serum or plasma. Where quantitative results are desired, steps generally similar to those outlined hereinabove are followed.

Thus, a known amount of a liquid sample to be assayed is admixed with a solid support that consists essentially of a solid matrix having solid phase-bound first monoclonal paratopic molecules that immunoreact with apolipoprotein A-I and are secreted by one of the hybridomas having ATCC accession numbers HB 9200 or HB 9201 to form a solid-liquid phase admixture. The non-specific protein binding sites on the surface of the solid support are blocked. The solid-liquid phase admixture is maintained under biological assay conditions for a predetermined period of time sufficient for the first paratopic molecules to immunoreact with substantially all of the apolipoprotein A-I present in the sample.

The apolipoprotein A-I of the above liquid sample is further admixed with liquid phase second monoclonal paratopic molecules that immunoreact with apolipoprotein A-I, are secreted by one of the hybridomas having ATCC accession numbers HB 9200 or HB 9201 but are not utilized in the first-named admixture, and are operatively linked to an enzyme indicating means to form a second admixture. Thus, the paratopic molecules utilized in this step are the other of the two named in the first admixing step.

The second admixture so formed is maintained under biological assay conditions for a predetermined period of time sufficient for the second indicating means-linked paratopic molecules to form an immunoreactant with substantially all apolipoprotein A-I present in this sample. The solid and liquid phases that result from the above admixtures and maintenance steps are separated, and the amount of indicating means-linked apolipoprotein A-I-containing immunoreactant present in the separated solid phase, and thereby the amount of apolipoprotein A-I in the sample, is determined.

It is particularly preferred that the two admixing steps of the above assay method be carried out substantially simultaneously, and that the two maintaining steps be carried out together. Where those steps are not carried out substantially simultaneously and together, respectively, it is preferred that the solid and liquid phases present at the end of the first maintenance step be separated prior to the second admixture, in which case the apolipoprotein A-I utilized in the second admixture is that present in the solid phase-bound immunoreactant formed in that first maintenance step.

A diagnostic system typically in kit form that is suitable for use in determining the presence of apolipoprotein A-I in a liquid sample constitutes another aspect of the present invention. In one embodiment, the system comprises a package that contains paratopic molecules secreted by one of the before-discussed hybridomas present in an amount sufficient to carry out at least one assay. More preferably, the diagnostic system further includes an indicating means that is operatively linked directly to the above paratopic molecule or linked to another molecule that is capable of signalling the immunoreaction of the above paratopic molecules with apolipoprotein A-I.

Most preferably, the diagnostic system is suitable for use in determining the amount of apolipoprotein A-I present in a liquid blood sample. That diagnostic system comprises a first package containing a solid support that consists essentially of a solid matrix having monoclonal paratopic molecules that immunoreact with apolipoprotein A-I and are secreted by one of the hybridomas having ATCC accession numbers HB 9200 or HB 9201 bound to the solid matrix. The non-specific protein binding sites of that solid support are blocked. This system further includes a second package that contains paratopic molecules that immunoreact with apolipoprotein A-I, are secreted by one of the hybridomas having ATCC accession numbers HB 9200 or HB 9201 but are not secrected by the hybridoma of the first package, and are operatively linked to an enzyme indicating means.

The present invention has several benefits and advantages.

One of those benefits and advantages is that it provides reagents that are capable of immunoreacting with substantially all of apolipoprotein A-I or HDL particles in a liquid blood sample such as serum or plasma.

Another benefit and advantage of the present invention is that use of those paratopic molecules can provide a qualitative assay for the presence of apolipoprotein A-I or HDL.

Still another benefit and advantage of the present invention is that through use of particularly preferred paratopic molecules secreted by two of the hybridomas of the invention, a highly accurate and precise assay can be performed to quantify the amount of apolipoprotein A-I present in a blood sample.

Still further benefits and advantages of the present invention will be apparent to those skilled in the art from the detailed description of the invention that follows.

The graph illustrates that increasing amounts of unlabeled AI-10 molecules in the immunoreaction admixture correspondingly decrease the amount of labeled AI-10 bound as the solid phase immunoreactant. Thus, unlabeled AI-10 competes with labeled AI-10 for apo A-I.

The graph also illustrates that increasing amounts of unlabeled AI-11 molecules do not significantly decrease the amount of labeled AI-10 molecules bound as solid phase immunoreactant. Thus, unlabeled AI-11 molecules do not compete with labeled AI-10 molecules for binding to apolipoprotein A-I.

Figure 1:
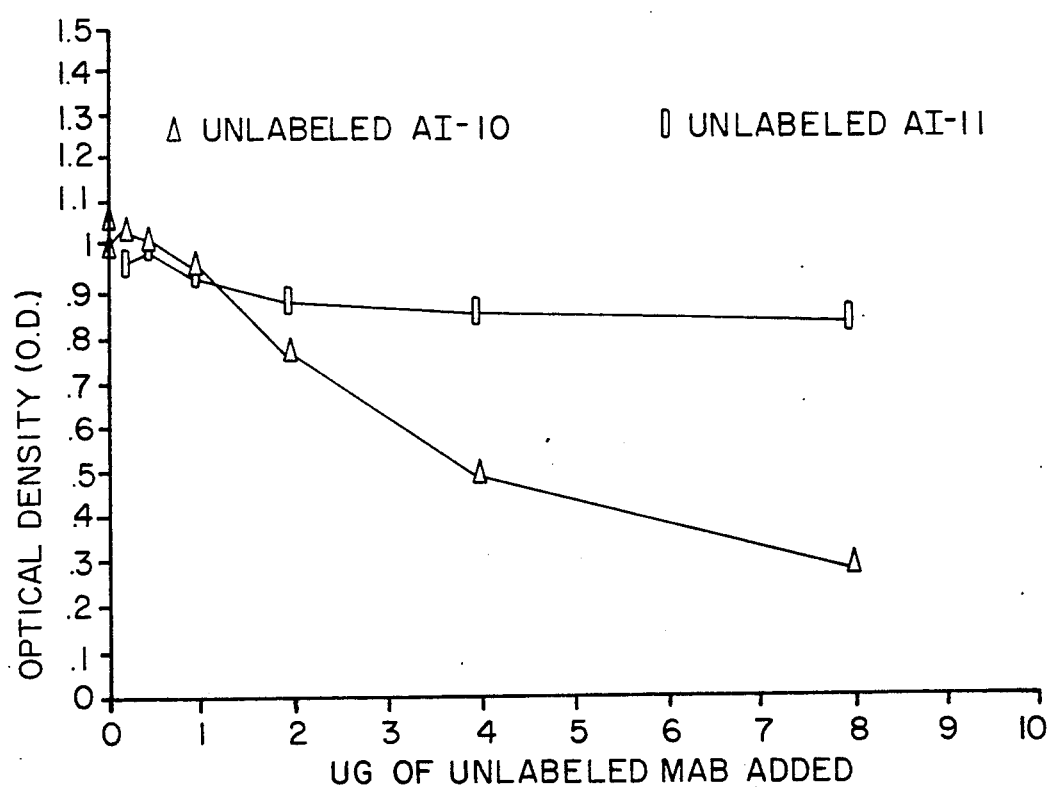
FIG. 1 contains a graph that illustrates the ability of a known, constant amount (0.375 ug/ml) of horseradish peroxidase (HRPO)-labeled AI-10 molecules to immunoreact with solid phase-affixed reagent apolipoprotein A-I in the presence of increasing amounts of unlabeled AI-10 ( ) and AI-11 ( ) molecules. The ordinate is in optical density units, whereas the abscissa is in units of micrograms (ug) of unlabeled competing monoclonal antibodies added. Details of this study are provided in the Materials and Methods Section.
Figure 2:
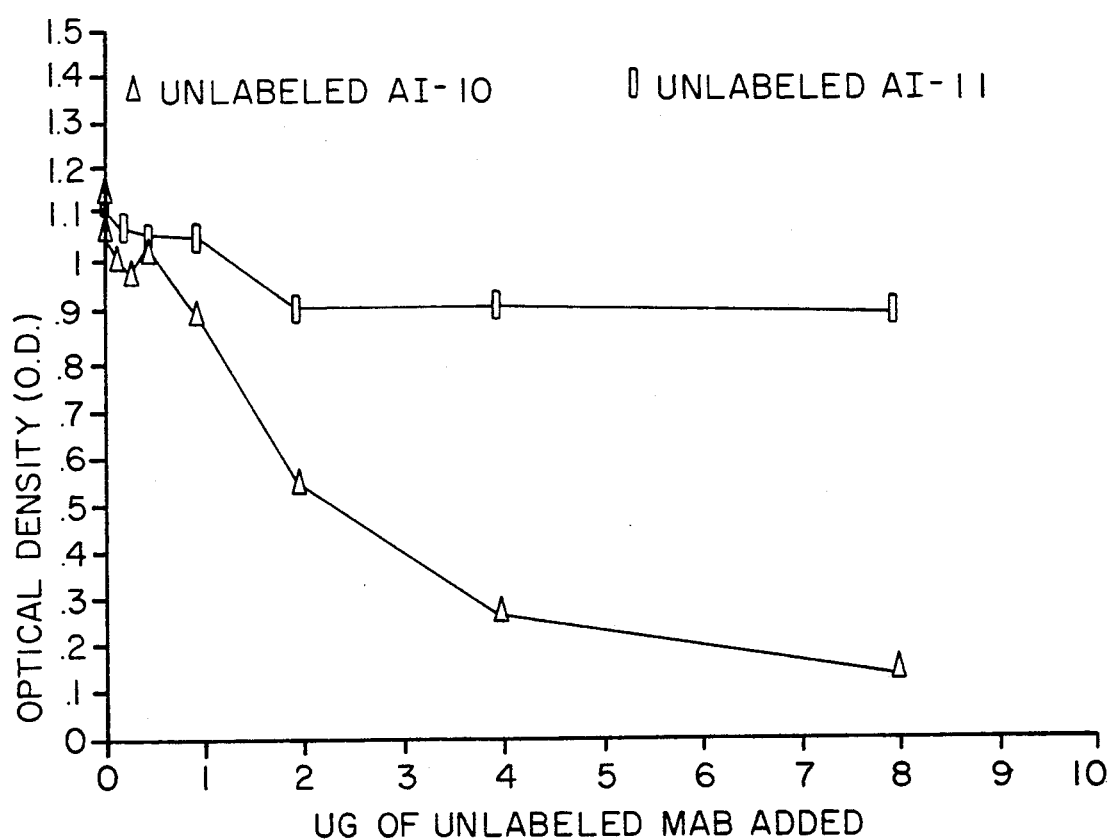

FIG. 2 contains a graph that illustrates that similar results are obtained to those of FIG. 1 using HDL as solid phase-bound antigen with a constant amount (0.375 ug/ml) HRPO-labeled AI-10 molecules and unlabeled AI-11 molecules ( ) and AI-10 molecules ( ). AI-10 and AI-11 molecules therefore bind to different epitopes that are sufficiently separated on the surface of apolipoprotein A-I or HDL so as to permit binding of both monoclonal antibody molecules to a single apo A-I molecule without sterically competing with and inhibiting the other's binding.

DETAILED DESCRIPTION OF THE INVENTION

I. Discussion

A. Definitions

The term "antibody" refers to a molecule that is a member of a family of glycosylated proteins called immunoglobulins that can specifically combine with an antigen. Such an antibody combines with its antigen by a specific immunologic binding interaction between the antigenic determinant of the antigen and the antibody combining site of the antibody.

An "antibody combining site" is that structural portion of an antibody molecule comprised of heavy and light chain variable and hypervariable regions that specifically binds antigen. Using the nomenclature of Jerne, (1974) *Ann. Immunol. (Inst. Pasteur)*, 125C:373–389, an antibody combining site is usually referred to herein as a "paratope".

Antibody combining site-containing (paratope-containing) polypeptide portions of antibodies are those portions of antibody molecules that contain the paratope and bind to an antigen, and include, for example, the Fab, Fab', F(ab')$_2$ and F(v) portions of the antibodies. Fab and F(ab')$_2$ portions of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. Intact antibodies are preferred, and are utilized as illustrative of the monoclonal ligand molecules of this invention.

The word "antigen" has been used historically to designate an entity that is bound by an antibody, and also to designate the entity that induces the production of the antibody. More current usage limits the meaning of antigen to that entity bound by an antibody, while the word "immunogen" is used for the entity that induces antibody production. Where an entity discussed herein is both immunogenic and antigenic, it will generally be termed an antigen.

The phrase "antigenic determinant" refers to the actual structural portion of the antigen that is immunologically bound by an antibody combining site. The Jerne nomenclature redefines an antigenic determinant as an "epitope".

The term "biologically active" refers at least to the ability of a proteinaceous molecule to specifically bind antigen or specific antibody combining site, although other general or effector capability may also be present in that molecule. Biological activity of a paratopic molecule containing an antibody combining site is evidenced by the immunologic reaction of the paratope (antibody combining site) with its epitope (antigenic determinant) upon their admixture in an aqueous medium to form an immunoreactant, at least at physiological pH values and ionic strengths. Preferably, biological activity occurs under biological assay conditions; i.e., those conditions wherein a monoclonal paratopic molecule useful in this invention binds to the epitope (antigenic determinant) within a pH value range of about 5 to about 9, at ionic strengths such as that of distilled water to that of about one molar sodium chloride. and at temperatures of about 4 degrees C. to about 45 degrees C. The monoclonal paratopic molecules useful herein are all biologically active.

"ELISA" refers to an enzyme-linked immunosorbent assay that employs an antigen or antibody bound to a solid phase and an enzyme-antibody or enzyme-antigen conjugate to detect and quantify the amount of antigen or antibody present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090; 3,850,752; and 4,016,043, which are incorporated herein by reference.

"Enzyme" refers to a protein capable of accelerating or producing by catalytic action some change in a substrate for which it is often specific.

"Immunoreactant" as used herein refers to the product of an immunological reaction; i.e., that entity produced when an antigen is immunologically bound by an antibody or a molecule containing a paratope. An immunoreactant is therefore a specific type of complex formed between molecules.

The terms "indicating means", "enzyme indicating means" or "label" are interchangeably used herein in various grammatical forms to include single atoms, molecules and enzymes that are either directly or indirectly involved in the production of a detectable signal to indicate their presence. Substantially any indicating means that can be linked to or incorporated into an antibody is useful herein, and those indicating means can be used alone or in conjunction with additional reagents. Such indicating groups or labels are themselves well-known in immunochemistry and constitute a part of this invention only insofar as they are utilized with otherwise novel paratopic molecules, methods and/or systems. Paratopic molecules when linked to an enzyme indicating means are sometimes referred to herein as being enzyme-linked paratopic molecules.

The term "whole antibody" is used herein to distinguish a complete, intact molecule secreted by a cell from other, smaller, molecules that also contain the paratope necessary for biological activity in an immunoreaction with an epitope.

The paratopic molecules of the present invention are monoclonal paratopic molecules. A "monoclonal antibody" (Mab) is an antibody produced by clones of a hybridoma that secretes but one kind of antibody molecule, and a monoclonal paratopic molecule is a monoclonal antibody or a paratope-containing polypeptide portion thereof, as is discussed below. The hybridoma cell is fused from an antibody-producing cell and a myeloma or other self-perpetuating cell line. Such antibodies were first described by Kohler and Milstein, *Nature*, 256, 495–497 (1975), which description is incorporated herein by reference.

The terms "monoclonal paratopic molecule" and "paratopic molecule" alone are used interchangeably and collectively herein to refer to the genus of molecules that contain a combining site of a monoclonal antibody, and include a whole monoclonal antibody, a substantially whole monoclonal antibody and an antibody binding site-containing portion of a monoclonal antibody. The whole monoclonal antibodies designated AI-10 and AI-11, AI-12, AI-13 and AI-14 are paratopic molecules of this invention as are portions of those whole antibodies that include the paratope. The terms "monoclonal paratopic molecule" or "paratopic molecule" are used alone herein when a generic biolgically active molecule containing the antibody binding site of the above monoclonal antibodies is intended, whereas the terms AI-10, AI-11, AI-12, AI-13 and AI-14 with and without the words "paratopic molecule" are used where the specific whole antibodies produced by hybridomas HB 9200, HB 9201, HB 9202, HB 9203 or HB 9204 are intended.

The words "secrete" and "produce" are often used interchangeably in the art to refer to cells from which antibody molecules are obtained. Cells that produce antibodies may, however, not secrete those molecules into their environment. The hybridoma cells of interest herein secrete monoclonal antibodies into their environment. Nevertheless, such cells are sometimes referred to herein as "antibody-producing" cells, and their antibodies are sometimes referred to as being "produced" in keeping with the phrase utilized in the art. Paratope-containing polypeptide portions of the above antibodies are similarly referred to herein as being "produced" or "secreted", although it is to be understood that such molecules are prepared from antibodies that are themselves "produced" or "secreted".

The terms "supernate" and "supernatant" are used interchangeably herein and refer to the in vitro liquid medium in which cells are cultured. Monoclonal antibodies produced by the hybridoma cultures of interest herein are secreted into their culture medium environment. Therefore the culture medium supernate for those cells is one preferred source of the monoclonal paratopic molecules and is readily obtainable free from hybridoma cells by well known techniques. Exemplary of such techniques is low speed centrifugation to sediment cells out of the liquid medium. Monoclonal paratopic molecules can alternatively be obtained from ascites tumor fluid (ascites fluid) of laboratory animals into which the hybridoma tissue was introduced. Both methods are described hereinafter.

The phrase "substantially simultaneously" as used herein in relation to the admixture of three or more antigen and paratopic molecule components to form an immunoreaction admixture means that all of the components are present and admixed in a single admixture within about 15 minutes of each other, and preferably within about 5 minutes of the admixture of any two of the components.

The phrase "substantially all" as used herein in relation to the immunoreaction of a paratopic molecule and its antigen apolipoprotein A-1 to form an immunoreactant means that the paratopic molecule immunoreacts with about 90 percent of the antigen present in solution to form the immunoreactant when the paratopic molecule is present in excess.

B. Hybridomas and Monoclonal Paratopic Molecules

The present invention contemplates paratopic molecules that are secreted by five hybridomas. Those paratopic molecules immunoreact with apolipoprotein A-I. The apolipoprotein A-I molecule is also frequently referred to herein as apo A-I.

Of the five hybridomas, those that bear the laboratory designations H91H4.2H8 and H103D8.1D11, and secrete paratopic molecules designated AI-10 and AI-11, respectively, are particularly preferred. Each of paratopic molecules AI-10 and AI-11 immunoreacts with a conserved antigenic determinant on apolipoprotein A-1 and immunoreacts with at least about 90 percent of 125I-HDL particles in a fluid phase RIA. As is seen from examination of FIGS. 1 and 2, both paratopic molecules AI-10 and AI-11 bind to apo A-I, but do not substantially interfere with each others' binding.

Each of the five hybridomas was deposited with the American Type Culture Collection (ATCC), Rockville, Md., on Sep. 16, 1986 in accordance with the Budapest Treaty on the International Recognition of the Deposit of Microorganisms for the Purposes of Patent Procedure. The laboratory designations, paratopic molecule designations and their classes, as well as the ATCC accession numbers are provided below.

| Laboratory Hybridoma Designation | Paratopic Molecule Designation | IgG Class | ATCC Accession Number |
| --- | --- | --- | --- |
| H91H4.2H8 | AI-10 | 2a | HB 9200 |
| H103D8.1D11 | AI-11 | 1 | HB 9201 |
| H105C7.1C10 | AI-12 | 1 | HB 9202 |
| H105F4.1B4 | AI-13 | 1 | HB 9203 |
| H114D12.2D8 | AI-14 | 2a | HB 9204 |

The above deposits were made in compliance with the Budapest Treaty requirements that the duration of the deposit should be for 30 years from the date of deposit or for 5 years after the last request for the deposit at the depository or for the enforceable life of a U.S. patent that matures from this application, whichever is longer. The hybridomas will be replenished should they become non-viable at the depository, and will be made available to the public by the ATCC upon the issuance of a patent from this application.

Curtiss and Edgington (1985) *J. Biol. Chem.*, 260:2982-2993 reported on the immunochemical heterogeneity of human HDL, as well as reporting the preparation of three hybridomas whose monoclonal paratopic molecules immunoreacted with apo A-I. Those monoclonal paratopic molecules designated AI-4, AI-7 and AI-9 each immunoreacted with human apo A-I and human HDL particles in fluid phase RIAs, but exhibited differing levels of immunoreactivity.

The studies reported in that paper indicated fluid phase, RIA indirect immunoprecipitation immunoreactivities with $^{125}$I-HDL in antibody excess as percentages of total trichloracetic acid-precipitable radiolabel of: AI-4 about 44%; AI-7 about 61%; and AI-9 about 32%. Maximal immunoreaction of AI-4, AI-7 and AI-9 to isolated $^{125}$I-apo A-I in fluid phase RIAs were reportedly about 60% for AI-4 and AI-7, and about 30% for AI-9.

Combinations of two or three of those monoclonal paratopic molecules failed to immunoprecipitate 100 percent of the labeled HDL. However, combinations of any two of those mononclonal paratopic molecules with monoclonal paratopic molecules to apolipoprotein A-II were successful in immunoreacting with 100 percent of the precipitable $^{125}$I-HDL.

As is discussed hereinafter in the Results Section, the immunoreactivities of the presently disclosed hybridomas with both human HDL and human apo A-I are considerably improved over those reported in Curtiss and Edgington (1985) *J. Biol. Chem.*, 260:2982-2993. These maximal immunoreactivities to HDL in a fluid phase RIA are about 30 or more percent greater than that reported for AI-7 that reportedly immunoreacted with about 60% of $^{125}$I-HDL.

The hybridomas of this invention were prepared from three separate fusions of mouse splenocytes with cells of the non-secreting mouse myeloma line P3x63Ag8.653. Fresh native or fresh glutaraldehyde-cross-linked human HDL were used as the immunogens.

C. The Methods

In accordance with the method aspect of the present invention, the presence and, if desired, amount of apolipoprotein A-I in a liquid sample is determined. The liquid sample is aqueous and can be water alone, a composition of salts, a buffer solution, or a body fluid such as a blood sample.

A liquid blood sample is often utilized in a method of this invention where a quantitative determination for apo A-I or HDL is desired. The sample can be either serum or plasma, as results obtained using both have been found to be statistically indistinguishable. Indeed, some results reported hereinafter using the method were obtained using averaged values obtained from assays of both serum and plasma. Regardless of whether serum or plasma is used, the liquid blood sample is preferably obtained from persons who have fasted for at least about 12 hours as is known in the art. Such a blood sample is referred to as a "fasting" sample. It is also noted that where serum or plasma is used as the liquid sample in a quantitative assay, that sample need not be subjected to an unmasking treatment as is usually carried out in the determination of apo A-I from such samples.

It was surprising that accurate and precise results could be obtained utilizing the particularly preferred ELISA methods described herein using a liquid blood sample such as plasma or serum because those sample materials contain proteins, lipids and other compounds that could be expected to interfere with the assay. See, for example, Maggio, *Enzyme-Immunoassay*, CRC Press, Inc. Boca Raton, Fla., 1980, page 65.

For quantitative measurements, the amount of apolipoprotein A-I is determined using a predetermined amount of liquid sample. Where the liquid sample is a liquid blood sample such as plasma or serum, an unmasking treatment as is usual for measurement of apo A-I is not required, and that sample can be used free of such unmasking treatments.

Where a qualitative assay is desired, it is not critical that the user know the volume of liquid sample utilized. Of course, however, the sample volume and apo A-I concentration utilized should not be so great as to overwhelm the reagents utilized, nor should they be so small that the presence of an unrealistically small amount of apo A-I is sought. For example, accurate and precise quantitative determinations are routinely made in an ELISA method, using samples that contain about 10 to about 200 nanograms of apo A-I. Thus, qualitative determinations can be made at still lower amounts of apo A-I.

Broadly, the method comprises the steps of admixing a liquid sample to be asayed with an effective amount of paratopic molecules selected from the group consisting of the before-mentioned five monoclonal paratopic molecules to form an admixture. That admixture is maintained under biological assay conditions for a predetermined period of time sufficient for the paratopic molecules to immunoreact with apolipoprotein A-I present in the sample and form an immunoreactant. The presence of the immunoreactant is thereafter determined, thereby determining the presence of apolipoprotein A-I in the original sample.

It is to be understood that the above assay can be a solid or liquid phase assay, or any other immunoassay, as are well known. Exemplary liquid and solid phase assays are illustrated hereinafter. In addition, for solid phase asays, either competing apo A-I (HDL) or the paratopic molecules can be bound to the solid phase.

The presence of the immunoreactant can be determined in a number of ways, each of which typically utilizes an indicating means as described herein.

In this aspect of the invention, however, the paratopic molecules preferably contain an operatively-linked radioactive element as an indicating means, and the presence of apolipoprotein A-I in the original sample is determined by separating the immunoreactant from the remainder of the admixture and assaying for emitted radiation of the separated immunoreactant.

In another embodiment of the assay method, the first-named monoclonal paratopic molecules are bound to a solid matrix to form a solid support prior to the admixture. The non-specific protein binding sites of that solid support are blocked. The immunoreactant that is formed after admixture is bound to the solid support as a solid phase-bound immunoreactant. In this embodiment, it is preferred that the presence of a solid phase-bound immunoreactant be determined by the use of indicating means-containing molecules that are second monoclonal paratopic molecules, as is discussed hereinafter. Here, liquid phase indicating means-containing molecules are admixed with the above, first-named admixture to form a second admixture.

Those indicating means-containing molecules immunoreact with a second epitope of apolipoprotein A-I that is not substantially blocked by the immunoreaction of first-named monoclonal paratopic molecules, and are selected from the before-mentioned monoclonal paratopic molecules, but are not those molecules utilized in the first-named admixture. A particularly useful pair of monoclonal paratopic molecules are those secreted by hybridomas having ATCC accession numbers HB 9200 and HB 9201. Those second paratopic molecules are operatively linked to an indicating means that is preferably an enzyme. The linked indicating means can be any indicating means as discussed herein.

The second admixture so formed is maintained under biological assay conditions for a predetermined period of time sufficient for the second indicating means-linked paratopic molecules to immunoreact with apolipoprotein A-I present in the admixture. The solid and liquid phases formed after the admixture of both paratopic molecules, and the formation of their immunoreactants are separated. The presence of indicating means-linked apolipoprotein A-I in the separated solid phase is determined, thereby determining the presence of apolipoprotein A-I in the sample. The immunoreactant formed between a solid phase-bound paratopic molecule, the apo A-I antigen and label-linked second paratopic molecule is sometimes referred to herein as a sandwich immunoreactant.

The monoclonal paratopic molecules of the present invention are also useful in quantitative assays for the amount of apolipoprotein A-I in a liquid sample, particularly in a liquid blood sample such as serum or plasma, as noted previously. Where quantitative results are desired, steps generally similar to those outlined hereinabove for the solid phase assay are followed.

Thus, in the quantitative analysis for the amount of apolipoprotein A-I, a first solid-liquid phase admixture is formed by admixing a predetermined, known amount of a liquid sample such as plasma or serum that is free from an unmasking treatment with a solid support that consists essentially of a solid matrix having solid phase-bound first monoclonal paratopic molecules that immunoreact with apo A-I. Those solid phase-bound first monoclonal paratopic molecules are present in excess over the amount of apo A-I expected in the sample, and are secreted by one of the hybridomas having ATCC accession numbers HB 9200 or HB 9201. Non-specific protein binding sites on the surface of that solid support are blocked prior to that admixture.

That first solid-liquid phase admixture is maintained under biological assay conditions for a predetermined period of time that is sufficient for the first paratopic molecules to immunoreact with apolipoprotein A-I present in the sample aliquot and form a solid phase-bound immunoreactant that contains substantially all apolipoprotein A-I present in the sample.

The apo A-I of the sample also is admixed with liquid phase second monoclonal paratopic molecules that immunoreact with apolipoprotein A-I to form a second admixture. Those second monoclonal paratopic molecules are secreted by one of the hybridomas having ATCC accession numbers HB 9200 or HB 9201, but are not utilized in the first-named admixture. Those second paratopic molecules also are operatively linked to an enzyme indicating means. Thus, the paratopic molecules used in this step are the other of the two paratopic molecules named in the above, first, admixing step.

The second admixture so formed is maintained under biological assay conditions for a predetermined period of time sufficient for the second, enzyme-linked paratopic molecules to form a sandwich immunoreactant that contains substantially all apolipoprotein A-I in the sample aliquot.

The solid and liquid phases that result from admixture of both paratopic molecules and formation of immunoreactants between both paratopic molecules and apo A-I are separated as by rinsing, and the amount of indicating means-linked apolipoprotein A-I-containing sandwich immunoreactant present in the separated solid phase is determined. Because each of the two monoclonal paratopic molecules immunoreact with substantially all of the apo A-I present in the sample aliquot, and because at least one of the paratopic molecules immunoreacts with a non-cross-reactive, conserved epitope on apo A-I, determination of the amount of enzyme-linked apo A-I in the immunoreactant provides a determination of the amount of apolipoprotein A-I present in the sample aliquot. The amount of apolipoprotein A-I in the sample can readily be calculated by knowledge of the volume of the originally utilized, predetermined amount, of liquid sample aliquot.

The solid phase assays for apolipoprotein A-I discussed above can each be carried out with each of the admixing and maintaining steps in each assay being carried out sequentially, or the two admixing steps in each assay can be carried out substantially simultaneously with the two maintaining steps in each assay being carried out together, as already noted.

When the steps are carried out sequentially, it is preferred that the solid phase-bound monoclonal paratopic molecules be admixed and the formed admixture maintained prior to admixture of the enzyme indicating means-linked paratopic molecules and maintenance of that resulting admixture. When the preferred, sequential steps are followed, it is further preferred that the solid and liquid phases formed be separated, and the solid phase rinsed to help assure that separation, prior to the admixture of the liquid enzyme indicating means-linked paratopic molecules to the separated solid phase and maintenance of that admixture.

It is also noted that the enzyme indicating means-linked paratopic molecules can be the first admixed with the appropriate sample. When this mode of carrying out the method is utilized there is no separating of phases prior to admixture of the solid phase-bound monoclonal paratopic molecules.

Most preferably, the solid phase-bound monoclonal paratopic molecules, liquid sample and enzyme indicating means-linked paratopic molecules are separately admixed substantially simultaneously, and the resulting solid-liquid phase admixtures is maintained together. Thus, the admixture is maintained for a period of time sufficient for the solid phase-bound monoclonal paratopic molecules to form solid phase-bound immunoreactants with substantially all of the apo A-I and for the liquid phase enzyme indicating means-linked paratopic molecules to also immunoreact with substantially all of the apo A-I in the sample. The immunoreactant so formed is referred to as a solid phase-bound sandwich immunoreactant. A liquid phase is also present.

Similar results are obtained using either of the two monoclonal paratopic molecules as the solid phase-bound paratopic molecules in the respective assays. However, most of the work discussed herein was carried out using the molecules secreted by the hybridoma having ATCC accession No. HB 9200 (AI-10) bound to the solid phase matrix for the assay of apolipoprotein A-I.

Exemplary solid matrices useful in the above methods are well known in the art and include a solid matrix such as a 96-well microtiter plate sold under the designation Falcon Microtest III Flexible Assay Plates (Falcon Plastics, Oxnard, CA) or a microtiter strip containing twelve wells in a row, such as those strips sold under the designation Immulon I and II (Dynatech, Alexandria, Va.). The microtiter strip or plate is made of a clear plastic material, preferably polyvinylchloride or polystyrene. Alternative solid matrices for use in a before-described method of this invention include polystyrene beads, about 1 micron to about 5 millimeters in diameter, available from Abbott Laboratories, North Chicago, Ill.; polystyrene tubes, sticks or paddles of any convenient size; and polystyrene latex whose polystyrene particles are of a size of about 1 micron and can be centrifugally separated from the remainder of the latex.

The solid matrix also can be made of a variety of materials such as cross-linked dextran, e.g. Sephadex G-25, -50, -100, -200 and the like available from Pharmacia Fine Chemicals of Piscataway, NJ, agarose and cross-linked agarose, e.g. Sepharose 6B, CL6B, 4B, CL46 and the like also available from Pharmacia Fine Chemicals.

The indicating means can be linked directly to a paratopic molecule of this invention, to a useful antigen, or can comprise a separate molecule. The indicating means can be a separate molecule such as antibodies that bind to paratopic molecules of this invention such as goat or rabbit anti-mouse antibodies. Staphylococcus aureus protein A, sometimes referred to herein as protein A, also can be used as a separate molecule indicator or labelling means where whole or substantially whole paratopic molecules of this invention are utilized; i.e., where a molecules containing the portion of the Fc regions of paratopic molecules that are bound by protein A are used. In such uses, the protein A itself contains a label such as a radioactive element or a fluorochrome dye.

Radioactive elements provide a class of label that is particularly useful. An exemplary radiolabelling agent that can be utilized in the invention is a radioactive element that produces gamma ray emissions. Elements that themselves emit gamma rays such as $^{124}I$, $^{125}I$, $^{128}I$, $^{131}I$, $^{132}I$ and $^{51}Cr$ represent one class of gamma ray emission-producing radioactive element indicating groups. Another class of useful indicating groups are those elements such as 11C, 18F, 15O and 13N which themselves emit positrons. The positrons so emitted produce gamma rays upon encounters with electrons present in the admixture.

A radioactive monoclonal paratopic molecule can typically be made by isolating the monoclonal paratopic molecule and then labelling the paratopic molecule with one of the above or another appropriate radioactive elements as described in U.S. Pat. No. 4,381,292. An exemplary indicator labelling means is a fluorescent labelling agent that can be chemically linked to antibodies or antigens without denaturing them to form a fluorochrome (dye) that is a useful immunofluorescent tracer. Suitable fluorescent labelling agents are fluorochromes such as fluorescein isocyanate (FIC), flourescein isothiocyanate (FITC), dimethylamino-naphthalene-S-sulphonyl chloride (DANSC), tetramethylrhodamine isothiocyanate (TRITC), lissamine rhodamine B200 sulphonyl chloride (RB 200 SC) and the like. A description of immunofluorescence analysis techniques is found in DeLula, "Immunofluorescence Analysis", in *Antibody As A Tool*, Marchalonis et al., eds., John Wiley & Sons, Ltd., pp. 189-231 (1982), which is incorporated herein by reference.

An enzyme is a particularly preferred indicating means. When used, the enzyme is preferably linked directly to a paratopic molecule of this invention to form a conjugate.

It is to be understood that useful enzyme molecules or other indicating means linked to a paratopic molecule are operatively linked. Thus, the function of the enzyme or other label is not substantially impaired by the linkage or by the paratopic molecule, nor is the function of the monoclonal paratopic molecule to which the enzyme or other label is linked substantially impaired by that linkage or the presence of the enzyme or other label.

The enzyme indicating means is a biologically active enzyme such as horseradish peroxidase (HRPO) or glucose oxidase, or the like. As is well known, where the indicating means is an enzyme such as HRPO or glucose oxidase, additional reagents are required to visualize the fact that a antibody-antigen complex has formed. Such additional reagents for HRPO include hydrogen peroxide and an oxidation dye precursor such as diaminobenzidine. Additional reagents useful with glucose oxidase include glucose and 2,2'azino-di-(3-ethylbenzthiazoline-6-sulfonic acid) (ABTS).

Techniques for operatively linking an enzyme to a paratopic molecule to form a conjugate are well known in the art. Exemplary techniques are discussed in Maggio, *Enzyme-Immunoassay*, Chapter 4 by Kabakoff, CRC Press, Boca Raton, Fla. (1980), pages 71-104.

The monoclonal paratopic molecules can be utilized as obtained from hybridoma supernatants or as ascites. However, it is preferred that purified paratopic molecules be utilized.

Several means for purification of paratopic molecules are well known in the art and typically utilize chromatographic techniques. Fast protein liquid chromatography (FPLC) is the purification technique of choice herein.

The enzyme-linked paratopic molecule conjugates are provided to the admixtures in the fluid phase. Those molecules are typically dissolved in an aqueous composition. Typical compositions contain buffer salts as is the case of the exemplary purified monoclonal antibody-containing compositions used herein that include phosphate-buffered saline (PBS) as a diluent. Diluted ascites fluid also is useful.

As noted before, non-specific protein binding sites on the surface of the solid phase support are blocked. Thus, the solid phase-bound paratopic molecules are bound as by adsorption or other well known means of affixation to the solid matrix. Thereafter, an aqueous solution of a protein free from interference with the assay such as bovine, horse or other serum albumin that is also free from contamination with human apo A-I is admixed with the solid phase to adsorb the admixed protein onto the surface of the paratopic molecule-containing solid support at protein binding sites on the surface that are not occupied by the monoclonal paratopic molecule.

A typical aqueous protein solution contains about 3 to about 10 weight percent bovine serum albumin in PBS at a pH value of 7.1-7.5. The aqueous protein solution-solid support admixture is typically maintained for a time period of at least one hour at 7 degrees C., and the resulting solid phase is thereafter rinsed free of unbound protein.

The liquid blood sample can be plasma or serum, as already noted. That sample is preferably diluted at a rate of about 1:2500 to about 1:20,000, and more preferably at about 1:5000, before use to obtain linear results in the assays specifically described hereinafter. The use of a lesser dilution can provide too much of the apolipoprotein antigen to the admixture and impair the linearity of the assay results as well as lower or abolish the solid phase-bound paratopic molecule excess over the admixed antigen. Use of greater than about a 1:20,000 dilution tends to decrease precision.

The maintenance times utilized can vary widely with little variance in result so long as a minimum time of about 30 minutes at ambient room temperature (about 20-25 degrees C.) is utilized. Where it is desired to use a minimum 30-minute maintenance time, it is preferred that the maintained admixture be agitated during that time period to assure substantially complete immunoreaction between the apolipoprotein A-I antigen and monoclonal paratopic molecules. Where longer maintenance times such as one hour or more at room temperature are utilized, agitation is not required. The desired agitation can be readily supplied by means of a gyroshaker operated at about 100 rpm. Each of the assays used in the quantitative method is capable of being carried out using paratopic molecule-sample admixture maintenance times of about 30 minutes to about 60 minutes at ambient room temperatures.

The amount of apolipoprotein A-I antigen present in the assayed immunoreactant is determined by admixture of the separated enzyme-linked apolipoprotein-containing solid phase with a predetermined amount of visualizing reagent or reagents. Where HRPO is utilized as the enzyme indicating means, visualizing reagents such as hydrogen peroxide and an oxidative dye precursor such as o-phenylenediamine (OPD) present in an aqueous medium are admixed with the separated solid phase-bound immunoreactant. The admixture so formed is maintained under biological assay conditions for a predetermined time such as at least about 30 minutes at ambient temperature for color to develop. Color development is thereafter stopped by admixture of a stopping reagent such as 4N sulfuric acid. The optical density of the composition is thereafter read, compared to a standard curve value, and the amount of apolipoprotein is determined, as is well known.

Thus, once the solid support and liquid blood sample are prepared, a quantitative assay can be carried out at ambient room temperature in a time period of about one hour; i.e., a 30-minute maintenance time with agitation for the admixture formed from paratopic molecules and the sample, and another 30-minute maintenance time for color development. Indeed, one need not prepare the solid support just prior to each use, but rather, such supports as are described herein can be prepared and stored damp and covered under usual refrigeration conditions for a period of at least one month prior to use.

The apo A-I quantitative assay utilizes a standard against which the optical density values obtained in the ELISAs are compared to calculate the concentrations of apolipoprotein. The assay utilizes a secondary standard. That is, rather than utilizing a specific HDL or apo A-I as standards, the assay utilize pooled human HDL as the standards. The secondary standards are utilized because of the relative instability of the primary apolipoprotein A-I or HDL on storage. Kottke and coworkers also noted degradation of purified apo A-I used as a primary standard, and utilized a secondary standard in their RIA with polyclonal serum for apo A-I. Au et al. (1986) *Clin. Chem.* 32:1394–1397.

The secondary standards are provided as lyophilized, pooled human fasting plasma containing HDL (apo A-I), and are reconstituted before use. Each of the standards is itself standardized against primary HDL or apo A-I standards. An exemplary procedure is illustrated for apolipoprotein A-I in the Materials and Methods Section.

D. Diagnostic Systems

The present invention also contemplates a diagnostic system, typically in kit form, that can be utilized in carrying out the before-described methods. The system includes a package that contains one of the before-described monoclonal paratopic molecules that immunoreact with apo A-I. The package contains an amount of those paratopic molecules sufficient to carry out at least one assay for apo A-I.

The assay system more preferably further includes an indicating means that is operatively linked directly to the above paratopic molecules or is linked to another molecule that is capable of signalling the immunoreaction of the above paratopic molecules with apo A-I.

Most preferably, the system is suitable for use in quantitatively determining the amount of apo A-I present in a liquid blood sample. Such a system comprises a first package containing a solid support that consists essentially of a solid matrix having bound monoclonal paratopic molecules that immunoreact with apo A-I and whose surface non-specific protein binding sites is blocked. The system further includes a second package that contains an enzyme-linked monoclonal paratopic molecule conjugate that immunoreacts with apo A-I. The same two paratopic molecules are utilized in this system as are discussed hereinabove in relative to the quantitative apo A-I determination.

The solid phase matrices of the above diagnostic system can be any of the solid phase matrices discussed before Microtiter wells such as those of the before-described 12-well strips and 96-well plates are particularly preferred. Non-specific binding sites on the solid supports are blocked as previously discussed.

The solid matrix can constitute a container for the solid phase-bound monoclonal paratopic molecules of this embodiment. Typical containers for the enzyme-linked monoclonal paratopic molecules are vials or bottles made from glass or a plastic such as polyethylene or polypropylene.

Using a microtiter plate as an exemplary solid matrix, and, whole monoclonal antibodies AI-10 as the solid phase-bound monoclonal paratopic molecules, serum as the liquid blood sample, and, whole monoclonal antibodies AI-11 linked to HRPO, an exemplary more preferred diagnostic system in kit form includes the following:

a) a solid support that consists essentially of a microtiter plate having monoclonal antibody AI-10 bound thereto in an amount sufficient to carry out an assay of a serum sample for the amount of apolipoprotein A-I present therein, and whose surface non-specific protein binding sites are blocked; and b) a separate package that contains an aqueous solution containing monoclonal antibody AI-11 operatively linked to HRPO that is present in an amount sufficient to carry out an assay of a serum sample for the amount of apo A-I present therein.

Most preferably, a diagnostic system includes the above components and one or more of the following: (i) a supply of hydrogen peroxide of known concentration; (ii) a visualizing oxidative dye precursor such as OPD; (iii) a solution of a stopping agent such as 4N sulfuric acid to quench the color-forming reaction; (iv) one or more buffers in dry or liquid form for use in the assay; (v) materials for preparing standard reference curves; and (vi) instructions for carrying out the assays. Each of the immediately above-enumerated components is present in the diagnostic system in an amount sufficient to carry out at least one assay, and those components are separately packaged as is appropriate.

II. Results

As noted previously, the paratopic molecules secreted by each of the deposited hybridomas immunoreact with both HDL and apo A-I. Typical results obtained in a liquid phase RIA for the immunoreaction of each of those monoclonal paratopic molecules with HDL and Apo A-I are illustrated in Tables 1A and 1B below, as percentages of total trichloroacetic acid-precipitable $^{125}$I-HDL.

TABLE 1A

Maximum Immunoprecipitation with $^{125}$I-HDL in Liquid Phase RIA (%)

| Monoclonal Paratopic Molecules[1] | Ascites[2] | FPLC-Ascites[2,3] | Supernatant[4] |
|---|---|---|---|
| AI-10 | 92.6 | 85.9 | 27.0 |
| AI-11 | 100.0 | 93.0 | 85.0 |
| AI-12 | 89.7 | 94.0 | 87.0 |
| AI-13 | 93.1 | 93.1 | 81.0 |
| AI-14 | 91.4 | 91.4 | 34.0 |

[1]Liquid phase paratopic molecules were admixed with liquid phase $^{125}$I-HDL or $^{125}$I-apo A-I.
[2]Mouse ascites fluid was used as the source of the recited paratopic molecules.
[3]Mouse ascites fluid purified by fast protein liquid chromatography (FPLC) was used as the source of the recited paratopic molecules.
[4]Supernatant from hybridoma cell culture was used as the source of the recited paratopic molecules.

TABLE 1B

Maximum Immunoprecipitation with $^{125}$I-Apo-I in Liquid Phase RIA (%)

| Monoclonal Paratopic Molecules[1] | Ascites[2] | FPLC-Ascites[2,3] | Supernatant[4] |
|---|---|---|---|
| AI-10 | 64.7 | 70.2 | 88.0 |
| AI-11 | 48.8 | 60.4 | 41.0 |
| AI-12 | 43.8 | 46.1 | 44.0 |
| AI-13 | 53.0 | 48.1 | 35.0 |
| AI-14 | 22.0 | 34.9 | 30.0 |

[1,2,3,4]See Table 1A footnotes.

As can be seen from the data in Table 1A, above, the paratopic molecules of the present invention immunoreact to a much greater extent with $^{125}$I-HDL than do the antibodies previously reported in Curtiss and Edgington (1985) *J. Biol. Chem.* 260:2982–2993. The above data also illustrate a generally enhanced immunoreactivity with $^{125}$I-apo A-I as compared to the immunoreactivities against the same antigen reported by Curtiss and Edgington. In addition, further work has indicated that the age of the standard can have a great effect upon the results obtained.

A study also was made using various combinations of the three anti-apo A-I and the anti-apo A-II monoclonals of Curtiss and Edgington as compared to AI-10 and AI-11 of the present invention in the ELISA measurement of apo A-I in blood samples. Most of those comparisons provided comparable results. However, several samples, and particularly blood samples from CAD patients, provided aberrant results as compared to the assay described herein and assays carried out by other techniques. Some of those comparable and aberrant results are shown in Table 2, below, for two combinations of the Curtiss and Edgington monoclonals.

TABLE 2

| | Comparative Apo A-I Levels Measured by ELISA[1] | | |
|---|---|---|---|
| Apo A-I Sample[2] | C&E Mab Com. 1[3] | C&E Mab Com. 2[4] | AI-10 AI-11[5] |
| 1 (105) | 46.0 | 49.0 | 84.3 |
| 2 (120) | 80.0 | 77.0 | 131 |
| 3 | 71.6 | N.D.[6] | 158 |
| 4 | 73.8 | N.D.[6] | 151 |
| 5 | 110 | 89.0 | 160 |
| 6 | 60.0 | 122 | 86.2 |
| 7 | 29.0 | 49.0 | 130 |
| 8 | 29.0 | 50.0 | 138 |
| 9 (159) | 151 | —[7] | 158 |

[1]Amounts of apo A-I in milligrams per deciliter as measured by ELISA using the general sandwich ELISA techniques discussed herein.
[2]Apo A-I-containing samples obtained commercially [#1 (Calbiochem-Behring), #2 (International Union of Immunological Standards; IUIS), #6 (Isolab electrophoresis sample), and #9 (Omega)]; from normal asymptomatic persons (#'s 3, 4 and 5); or CAD patients (#'s 7 and 8). Parenthesized numbers are the amount of apo A-I asserted to be present by the supplier.
[3]ELISA performed using a mixture of Curtiss and Edgington monoclonals (C&E Mab) AI-4, AI-7 and AII-1 bound to the solid matrix, and monoclonal AI-4 linked to HRPO as the indicating means-containing second monoclonal.
[4]ELISA as in footnote 3 using monoclonals AI-7, AI-9 and AII-1 bound to the solid matrix and HRPO-linked AI-4 as the second monoclonal.
[5]ELISA as in footnote 3 using monoclonal paratopic molecules of this invention. AI-10 was bound to the solid matrix, whereas HRPO-linked AI-11 was used as the second monoclonal paratopic molecule.
[6]N.D. = not done.
[7]Value obtained was above the range of the assay.

Whereas the above data indicate that use of the present paratopic molecules provides different results from those obtained using the Curtiss and Edgington antibodies in the aberrant samples, those data do not indicate which of the results is correct. The data summarized in Table 3, below, illustrate that the data obtained using the paratopic molecules of the present invention are correct for those aberrant samples as compared to those obtained using the Curtiss and Edgington antibodies.

The data summarized in Table 3 were obtained using serum and/or plasma from 30 normal, asymptomatic, persons (fifteen males and fifteen females) and the quantitative sandwich assay described herein. Assays also were carried out using two commercially available RIAs (RIA-I and RIA-II) and two commercially available RIDs (RID-I and RID-II). A sample from each donor was measured in each assay.

TABLE 3

| | Summary of Comparative Apo A-I Values Obtained Using Different Techniques[1] | | | | |
|---|---|---|---|---|---|
| | ELISA[2] | RIA-I[3] | RIA-II[4] | RID-I[5] | RID-II[6] |
| MEAN[7] | 155 | 114 | 139 | 175 | 186 |
| S.D.[8] | 39.4 | 28.7 | 32.6 | 40.6 | 17.6 |

[1]Apo A-I amounts in milligrams per deciliter.
[2]ELISA assay carried out as described in footnote 5 of Table 2, using serum and plasma.
[3]RIA-I utilized plasma, and was carried out with materials purchased from Isotex Diagnostics of Friendswood, TX, following the supplier's instructions.
[4]RIA-II utilized serum, and was carried out with materials purchased from Ventrex Laboratories, Inc. of Portland, ME, following the supplier's instructions.
[5]RID-I utilized plasma, and was carried out with materials purchased from Tago Inc. of Burlingame, CA following the supplier's instructions.
[6]RIA-I utilized serum, and was carried out with materials purchased from Calbiochem-Behring of La Jolla, CA, following the supplier's instructions.
[7]Mean of apo A-I values from all thirty samples assayed.
[8]S.D. = value of one standard deviation from the mean value.

As can be seen from the above summaries, the mean obtained using the present ELISA was about mid-way between the means obtained with the two RIAs (on the low side) and the two RIDs (on the high side). Thus, it appears from the general validity of result obtained using the present ELISA that the data in Table 2 obtained using AI-10 and AI-11 were indeed correct.

The assays of the present invention, like any other assays, utilize a standard. The ELISA assays can utilize a primary apo A-I or HDL standard, but for convenience and accuracy, a secondary HDL standard is utilized in preferred practice.

The secondary standard utilized is obtained from pooled fasting plasma from several donors. Here a pool of plasma from twenty donors is typically used. The secondary standard is itself standardized against a primary standard.

A primary apo A-I standard is usually not utilized because such standards have not been stable on storage. It is thought that the purified protein or glutamine or asparagine residues of the protein can be deaminated. The same is thought to occur with purified HDL when used as a primary standard.

To further validate data obtained using the secondary standard in quantitative ELISAs of this invention, a series of ELISAs was carried out using solid phase-bound AI-10 and HRPO-linked AI-11 with various commercially available apo A-I standards. Those results are shown in Table 4, below.

TABLE 4

| | Quantitative ELISAs Using Different Apo A-I Standards[1] | | | |
|---|---|---|---|---|
| Sample[2] | Secondary Apo-A-I[3] | Primary Std.-I[4] | Primary Std.-II[5] | Primary Std.-III[6] |
| 1 | 122 | 104 | 128 | 105 |
| 2 | 127 | 108 | 132 | 122 |
| 3 | 71.0 | 66.0 | 80.0 | 78.0 |
| 4 | 169 | 137 | 168 | 172 |
| 5 | 77.0 | 70.5 | 86.0 | 85.5 |
| 6 | 94.0 | 83.5 | 102 | 96.5 |
| 7 | 150 | 123 | 152 | 163 |
| 8 | 129 | 109 | 134 | 162 |
| 9 | 166 | 135 | 166 | 164 |
| 10 | 176 | 142 | 174 | 172 |
| 11 | 101 | — | — | 102 |
| 12 | 172 | — | — | 171 |
| 13 | 167 | — | — | 166 |
| 14 | 176 | — | — | 174 |
| 15 | 177 | — | — | 176 |
| 16 | 141 | — | — | 141 |
| 17 | 192 | — | — | 190 |

[1]Apo A-I amounts in milligrams per deciliter.
[2]Samples from laboratory preparations, as gifts or from commercial sources (#'s 1-11) or from normal, asymptomatic donors (#'s 12-17). It is noted that sample 12 was from the same person as sample 3 of Table 2, as was sample 15 from the same person as sample 5 of that Table.
[3]Secondary HDL standard as described herein.
[4]Primary Std.-I (primary standard I) was obtained from Meloy Laboratories of Springfield, VA.
[5]Primary Std.-II (primary standard II) was obtained from Scripps Laboratories of La Jolla, CA.
[6]Primary Std.-III (primary standard III) was obtained from Chemicon International, Inc. of El Segundo, CA.

As can be seen from a horizontal comparison of the data of Table 4, the results obtained with all of the standards were similar. The values obtained using the Meloy standard also can be seen to be generally somewhat lower than were the values obtained using the other standards. It is further noted that the value assigned by the supplier of the Meloy standard was about one-half of that found by an independent analysis.

A series of determinations was run over a period of about three months using the above commercial standards to ascertain the repeatability (coefficient of variation) of the quantitative assay of the present invention. The coefficient of variation was found to be about 11-13 percent.

In carrying out the assays of the present invention, indicating means-linked paratopic molecules that immunoreact with apo A-I are utilized to signal the immunoreaction of apo A-I with other monoclonal paratopic molecules. Since more than one apo A-I molecule is present per HDL particle, it is unclear whether it is necessary that the solid phase-bound paratopic molecules and the indicating means-linked paratopic molecules immunoreact with different epitopes on apo A-I to obtain an accurate and precise quantitative assay result. It is preferred, however, so long as both paratopic molecules are capable of immunoreacting with substantially all of the apo A-I or HDL of a sample, that each of the two types of monoclonal paratopic molecule be free from inhibiting the immunoreaction of the other monoclonal paratopic molecules.

As can be seen from the competitive immunoenzymometric data of FIGS. 1 and 2, HRPO-labeled AI-10 immunoreacts with apo A-I and HDL. The data of FIG. 1 illustrate that the immunoreaction of labeled AI-10 with apo A-I is inhibited by the presence of unlabeled AI-10, but not by the presence of unlabeled AI-11. FIG. 2 illustrates a similar result using HDL as the solid phase antigen. Comparable results also were obtained using HRPO-labeled AI-11 with unlabeled AI-10 and AI-11 with apo A-I and HDL as antigen.

Additional fluid phase binding studies using $^{125}$I-HDL and $^{125}$I-apo A-I were carried out using RIA techniques as described generally in Tsao et al. (1982) *J. Biol. Chem.* 257:15222-15228. The results of those studies are shown in Table 5, below, as percentages of total trichloracetic acid (TCA)-precipitable radioactivity.

A-I itself. That relative instability of apolipoprotein A-I has necessitated the use of a lyophilized plasma pool as a secondary standard in the apo A-I assay as was discussed before. The above data also illustrate a relatively lower binding of AI-11 to apo A-I than to HDL particles. Nevertheless, a comparison of data obtained utilizing the ELISA method for apo A-I with data obtained from the more laborious techniques as in Table 4 indicates that the ELISA method quantitatively detects substantially all of apo A-I (HDL) present in the samples assayed.

Further results obtained using the assay method described hereinbefore and in greater detail hereinafter in the Materials and Methods Section are discussed below. Wells of polystyrene 96-well microtiter plates were utilized as solid matrices. Whole monoclonal antibodies AI-10 were utilized as the solid phase-bound first monoclonal paratopic molecules. Non-specific protein binding sites on the solid support surfaces were blocked with BSA. HRPO-linked whole monoclonal antibodies AI-11 were utilized as the second and fourth monoclonal paratopic molecules, with OPD as the visualizing oxidative dye precursor.

Assays for apo A-I were carried out for 37 asymptomatic persons with no history of CAD. Those persons are referred to as "normals".

Apo A-I values were obtained using diluted plasma and serum as the liquid blood samples. Those values were found to show no statistically significant differences between the two sample sources and were averaged for use.

A summary of the results for the "normals" is shown in Table 6, below, for the 23 men and 14 women separately, and as "combined" values. A similar summary of apo A-I values obtained from the serum and plasma of 42 males who were clinically identified as having CAD is also shown in Table 6.

TABLE 6

| | Normal Apolipoprotein A-I Levels | | | |
|---|---|---|---|---|
| | | Normals | | |
| | Males[1] | Females[1] | Combined[1] | CAD Patients |
| | n = 23 | n = 14 | n = 37 | n = 42 |
| | mean = 143 | mean = 152 | mean = 147 | mean = 110 |
| | S.D. = 26.5 | S.D. = 10.7 | S.D. = 22.0 | S.D. = 28.8 |
| | S.D. Range = 116-170 | S.D. Range = 141-163 | S.D. Range = 125-169 | S.D. Range = 81.2-139 |

[1] "n" is the number of persons in each study. "mean" is the mean apo A-I value obtained expressed in milligrams per deciliter. "S.D." is the value of one standard deviation from the mean. "S.D. Range" is the breadth of one standard deviation on either side of the mean. Assays were carried out as described in the Materials and Methods Section.

TABLE 5

| | Fluid Phase Immunoreactivities of AI-10 and AI-11 | |
|---|---|---|
| Paratopic | Maximal Binding of Antigen (%) | |
| Molecules[1] | $^{125}$I-HDL[2] | $^{125}$I-Apo A-I[2] |
| AI-10 as: | | |
| Supernatant | 29.2 | 90.3 |
| Ascites | 92.6 | — |
| FPLC Ascites | 86.0 | 70.2 |
| AI-11 as: | | |
| Supernatant | 88.6 | 42.0 |
| Ascites | 100.0 | 49.0 |
| FPLC Ascites | 93.0 | 60.4 |

[1] Fluid phase paratopic molecules were used from hybridoma cell culture supernatant (Supernatant), mouse ascites fluid (Ascites), and fast protein liquid chromatography-purified ascites fluid (FPLC Ascites).
[2] Percentage of TCA-precipitable radioactivity.

The data of Table 5 illustrate the relatively high binding of whole AI-10 and AI-11 to radiolabeled HDL in the fluid phase assay utilized. Those data also reflect the relative instability of and resulting low binding to apo In reviewing the above data and comparing those data to the data provided in Kottke et al. (1986) *Mayo Clin. Proc.*, 61:313-320, it can be seen that the mean values for normal and CAD patients for apo A-I in the above assay are similar to those reported by Kottke et al. Similar standard deviations were obtained for both assay types.

This similarity of result was surprising for several reasons. First, the Kottke et al. workers used a detergent (Tween 20) unmasking treatment for their assays, whereas the present liquid blood samples were free of such treatments. Second, the Kottke et al. group utilized a radioimmunoassay, which is generally considered to be more accurate and precise than an ELISA as used herein. Voller et al. (1976) *Bull. World Health Organ.*, 53:55-65. Third, polyclonal antibodies that are normally considered capable of improved immunoreaction with the relatively heterogeneous apo A-I were used by Kottke et al., whereas monoclonal antibodies were used herein. Fourth, the Kottke et al. group utilized a maintenance time of 16 hours at room temperature for the immunoreaction of their polyclonal antibodies with apo A-I, whereas a time period of 30 minutes at room temperature was utilized herein.

III. Materials and Methods

A. Lipoproteins

In these studies, lipoproteins were isolated from plasma obtained by plasmaphoresis of normal fasting-donor blood at the local blood bank (San Diego Plasma Center, San Diego, Calif.). For that purpose, plasma so obtained was adjusted to contain a final concentration of 5 millimolar (mM) benzamidine, 1 mM diisopropyl flourophosphate, 10 mM ethylenediaminetetraacetic acid (EDTA), 10 milligrams per milliliter (mg/ml) soybean trypsin inhibitor and 10,000 units per ml aprotinin. The lipoproteins were then isolated from this adjusted plasma by sequential ultracentrifugation using solid potassium bromide (KBr) for density adjustment.

First, the adjusted plasma was centrifuged at about 200,000xg for 18 to 24 hours. Solid KBr was added to the bottom layer until the density was greater than 1.063 grams per milliliter (g/ml). The resulting composition was then layered under a 0.1% EDTA solution containing KBr at density of 1.063 g/ml and further centrifuged at 200,000xg for more than 48 hours.

The bottom layer was again recovered and to it was added solid KBr until the density was greater than 1.21 g/ml. That adjusted layer was layered under a 0.1% EDTA solution containing KBr at a density of 1.21 g/ml, and was further centrifuged at 200,000xg for more than 48 hours.

The top layer was then recovered and solid KBr was added until the density was greater than 1.063 g/ml. That adjusted top layer was layered under a 0.1% EDTA solution containing KBr at a density of 1.063 g/ml, and still further centrifuged at 200,000xg for more than 48 hours.

The middle layer was recovered and solid KBr was added to it until the density was greater than 1.21 g/ml. That adjusted middle layer was layered under a 0.1% EDTA solution containing KBr at a density of 1.21 g/ml and centrifuged at 300,000xg for more than 48 hours.

The top layer was recovered, designated high density lipoproteins (HDL) at a density equal to 1.063 to 1.21 g/ml. The recovered HDL was dialyzed against lipoprotein buffer (LLB) containing 150 mM NaCl, 1 mM EDTA, 0.005% alpha-tocopherol, and 5 mM benzamidine, and stored under sterile conditions for no more than 21 days.

B. Isolation of Apoprotein A-I

Apoprotein A-I (apo A-I) was purified from delipidated HDL (discussed hereinafter) by size fractionation using high pressure liquid chromatography (HPLC) following the procedures of Kinoshita et al. (1983) *J. Biochem.* 94:615–617. About 300 mg of ether:ethanol-delipidated HDL was dissolved in 200 microliters ($\mu$l) of 0.1% sodium dodecyl sulfate (SDS), 0.1M sodium phosphate (pH 7.0) and size fractionated on Spherogel - TSK 3000 SW HPLC columns (Beckman Instruments Inc., Fullerton, Calif.) fractions containing the purified Apo A-I were stored at minus 20 degrees C.

C. Generation of Monoclonal Paratopic Molecules

The five monoclonal paratopic molecules were obtained from three separate fusions of splenocytes from immunized Balb/c ByJ mice (Scripps Clinic and Research Foundation Vivarium, La Jolla, Calif.), using standard fusion protocols discussed herein. Culture supernates were collected and screened first by solid phase, and if positive, were rescreened by fluid-phase radioimmunoassay as described below. All hybridomas were cloned at least twice by limiting dilution, and were stored frozen in liquid nitrogen.

Briefly, Balb/c ByJ mice were immunized intraperitoneally (i.p.) with human HDL as immunogen in complete Freund's adjuvant (CFA) followed by a second and third immunization, each about three weeks apart, in incomplete Freund's adjuvant (IFA). For hybridoma AI-10 (ATCC HB 9200) only, the HDL was first cross-linked with glutaraldhyde, and then injected initially with 500 units of interferon-gamma (IFN-$\gamma$) in CFA, and without IFN-$\gamma$ in subsequent IFA immunization. The glutaraledhyde-cross-linked HDL was prepared by reacting fresh HDL in phosphate-buffered saline with glutaraldehyde at a final concentration of 0.04 percent at 20 degrees C. for a time period of 18 hours. For hybridomas AI-11, AI-12, AI-13 and AI-14 (ATCC HB 9201, HB 9202, HB 9203 and HB 9204) immunizations were with native HDL. In all cases, about three months after the last adjuvant-containing immunization, the mice received a prefusion boost of native HDL intravenously (i.v.) in normal saline and a second similar prefusion boost one day later.

The animals so treated were sacrificed about three days after the last boost, and the spleen of each mouse was harvested. A spleen cell suspension was then prepared. Spleen cells were then extracted from the spleen cell suspension by centrifugation for about 10 minutes at 1000 r.p.m., at 23 degrees C. Following removal of supernatant, the cell pellet was resuspended in 5 ml cold NH$_4$Cl lysing buffer, and was incubated for about 10 minutes.

To the lysed cell suspension were added 10 ml Dulbecco's Modified Eagle Medium (DMEM) (Gibco) and HEPES [4-(2-hydroxyethyl)-1-piperidineethanesulfonic acid] buffer, and that admixture was centrifuged for about 10 minutes at 1000 r.p.m. at 23 degrees C.

The supernatant was decanted, the pellet was resuspended in 15 ml of DMEM and HEPES, and was centrifuged for about 10 minutes at 1000 r.p.m. at 23 degrees C. The above procedure was repeated.

The pellet was then resuspended in 5 ml DMEM and HEPES. An aliquot of the spleen cell suspension was then removed for counting.

Fusions were accomplished in the following manner using the non-secreting mouse myeloma cell line P3x63Ag8.653.1, a subclone of line P3x63Ag 8.653 (ATCC 1580). Using a myeloma to spleen cell ratio of about 1 to 10 or about 1 to 5, a sufficient quantity of myeloma cells were centrifuged into a pellet, washed twice in 15 ml DMEM and HEPES, and centrifuged for 10 minutes at 1000 r.p.m. at 23 degrees C.

Spleen cells and myeloma cells were combined in round bottom 15 ml tubes (Falcon). The cell mixture was centrifuged for 10 minutes at 1000 r.p.m. at 23 degrees C., and the supernatant was removed by aspiration. Thereafter, 200 $\mu$l of 30 percent (weight per volume) aqueous polyethylene glycol 4000 molecular weight (PEG; ATCC Baltimore, MD) at about 37 degrees C. were added using a 1 ml pipette with vigorous stirring to disrupt the pellet, and the cells were gently mixed for between 15 and 30 seconds. The cell mixture was centrifuged 4 minutes at 700 r.p.m.

At about 8 minutes from the time of adding the PEG, 5 ml of DMEM plus HEPES buffer were added slowly to the pellet, without disturbing the cells. After 1 minute, the resulting admixture was broken up with a 1 ml pipette, and was incubated for an additional 4 minutes. This mixture was centrifuged for 7 minutes at 1000 r.p.m. The supernatant was decanted, 5 ml of HT (hypoxanthine/thymidine) medium were slowly added to the pellet, and the admixture was maintained undisturbed for 5 minutes. The pellet was then broken into large chunks, and the final cell suspension was placed into T75 flasks (2.5 ml per flask) into which 7.5 ml HT medium had been placed previously. The resulting cell suspension was incubated at 37 degrees C. to grow the fused cells. After 24 hours 10 ml of HT medium were added to the flasks, followed 6 hours later by admixture of 0.3 ml of 0.04 mM aminopterin. 48 Hours after fusion, 10 ml of HAT (hyoxanthine/aminopterin/thymidine) medium were added to the flasks.

Three days after fusion, viable cells were plated out in 96-well tissue culture plates at about $2 \times 10^4$ viable cells per well (768 total wells) in HAT buffer medium as described in Kennett et al., *Curr. Top. Microbiol. Immunol.*, 81:77 (1978). The cells were fed seven days after fusion with HAT medium and at approximately 4-5 day intervals thereafter as needed with HT medium. Growth was followed microscopically, and culture supernatants that contained antibodies were collected on day 14 for assay of HDL-specific antibody production by solid phase radioimmunoassay (RIA) as described in Curtiss and Edgington (1982) *J. Biol. Chem.* 257:15213-15221.

The hybridomas producing anti-HDL antibodies so prepared were screened, assayed, and their viabilities were determined. The present hybridomas were selected from about 30 hybridoma cultures that secreted anti-HDL antibodies into their culture media.

D. Paratopic Molecule Preparation and Purification

Ascites fluids were obtained from 10 week old Balb/c mice, which had been primed with 0.3 ml of mineral oil and injected intraperintoneally with $3 \times 50 \times 10^5$ hybridoma cells. The average time for development of ascites was 9 days. Following clarification by centrifugation at 15,000xg for 15 minutes at 23 degrees C, ascites fluids produced by each hybridoma were pooled and stored frozen at −20 degrees C.

Purified monoclonal paratopic molecules from each of the five hybridomas were prepared by fast protein liquid chromatography (FPLC) using a Pharmacia Mono Q HR5/5 anion exchange column (Pharmacia Fine Chemicals, Piscataway, N.J.) using a 0–0.5 molar (M) NaCl gradient in 10 mM Tris, pH 8.0 following directions supplied with the column. Purified Mabs were concentrated using an Amicon stirred ultrafiltration cell (Danvers, Mass.; PM 30 membrane) to a concentration of 1 mg/ml, dialyzed into PBS (phosphate-buffered saline, pH 7.2) and stored at −70 degrees C.

Monoclonal antibodies AI-4, AI-7, AI-9 and AII-1 were prepared as discussed in Curtiss and Edgington (1985) *J. Biol. Chem.* 260:2982-2993.

E. Radioiodination

Radioiodination of HDL, apo-A-I and immunochemically purified goat anti-mouse Ig was performed enzymatically utilizing the Enzymobead iodination procedure and Enzymobeads obtained from Biorad, (Burlingame, Calif.). The Enzymobead iodination was utilized to characterize the antigens and antibodies for the solid phase radioimmunoassay as discussed below.

G. Solvent Dilipidization of Lipoproteins

When needed, lipoproteins were delipidated by organic extraction and designated delipidated lipoproteins. For that purpose, the lipoprotein to be analyzed was dialyzed against 0.01 percent EDTA having a pH value of 7.5 overnight (approximately 18 hours).

The resulting sample was dialyzed against 0.003 percent EDTA for approximately 12 hours, and was then lyophilized at 10 to 20 milligrams of protein per tube. To each tube were added 35 ml of absolute ethanol:anhydrous ether (1:1) at 4 degrees C., and the resulting solution was mixed.

Following mixture, the solution was incubated for 20 minutes at −20 degrees C. The solutions were then spun for 30 minutes at 1000xg at zero degrees C., and the supernatant was poured off.

The ethanol ether extraction as described above was performed twice again for a total of three extractions. Then 35 ml anhydrous ether at 4 degrees C. were added to the sample and maintained for 30 minutes at −20 degrees C. The cold sample was spun at 1000xg for 30 minutes at −20 degrees centigrade, and the supernatant poured off and discarded. Pellets were dried using nitrogen gas.

H. Quantitative Apo A-I (HDL) Sandwich ELISA

1. Apo A-I Primary Standards: Quantitation of HDL and Isolated Apolipoprotein A-I The HDL fraction (1.063–1.21 g/ml) was obtained from pooled human plasma by standard ultracentrifugation techniques and was dialyzed into PBS. It was then sterile-filtered through a 0.45 micron acrodisc filter unit, and stored at 4 degrees C. The protein content of the HDL fraction was determined by a modified Lowry protein assay with BSA as the standard. Three dilutions of the HDL fraction were run in duplicate to assure readings within a linear part of the standard curve. For example, the HDL fraction was run at dilutions of 1:5, 1:10, and 1:20. Protein concentration was usually between 5 and 10 mg/ml. For extended storage, the HDL fraction was diluted with PBS to a protein concentration of 1-2 mg/ml. After dilution, the protein concentration was again confirmed by Lowry assay at dilutions of 1:2, 1:5, and 1:10. The diluted HDL fraction was then aliquoted and stored at 4 degrees C.

Isolated apolipoprotein A-I can be obtained from a number of commercial sources. Although, the manufacturer typically includes a statement of protein content and purity, the protein concentration was always confirmed by Lowry assay, and adjusted if necessary based on these results. Dilutions of the apo A-I preparation were run as described in the previous section. The preparation was aliquoted and stored as suggested by the manufacturer.

The HDL and/or apo A-I preparations were then assayed as unknown samples (diluted 1:5000) in the apo A-I ELISA (described hereinafter). A minimum of two assay plates per day, containing a complete set of standards, quality controls, and dilutions of the HDL and/or apo A-I preparations were performed over a five day period. The ELISA values obtained for HDL and/or apo A-I agreed within 20% of the Lowry protein assay value. If the values did not agree within the established limits, the Lowry assay was repeated to confirm the assigned protein concentration. If the values were still discrepant, aging or contamination of the preparation was usually indicated, and it is was not deemed suitable for use as a primary standard.

The purity of the primary standard also was determined by analytical sodium dodecyl sulfate-polyacrylamide gel electrophoresis; SDS-PAGE.

2. Apo A-I ELISA Secondary Standard Preparation and Value Assignment a. Preparation of Lyophilized Standard Pooled Plasma Fresh plasma or serum was collected from at least 10 normolipidemic subjects who had fasted overnight. Phelbotomy was performed using sterile tubes containing disodium EDTA by non-traumatic venipuncture. The samples were centrifuged at 1500xg for 30 minutes at 4 degrees C., and the plasma was transferred to clean, tightly capped tubes and stored for no more than 24 hours at 4 degrees C. Equal amounts of the samples were combined, and 0.5 ml quantities were aliquotted into acid-cleaned Wheaton 5 ml serum vials, and lyophilized overnight (about 16-18 hours). The vials were sealed and stored at 4 degrees C.

b. Reconstitution of Lyophilized Pooled Plasma Standard

Vials were allowed to come to room temperature before reconstitution. The aluminum ring and stopper were removed, slowly releasing the vacuum in the vial. Using a precision pipet, the dried, pooled standards were reconstituted with 0.5 ml double distilled water, by slowly dispensing the water to the side of the vials. The stoppers were replaced and the vials were quickly swirled 3-4 times and maintained at room temperature for at least 30 minutes. The standard was not vortexed or agitated strongly, but swirled gently to insure complete solubilization.

c. Value Assignment of the Apo A-I Secondary Standard

The apo A-1 value of the lyophilized secondary standard is determined in the apo A-I ELISA using the primary standard (either HDL or apo A-I) as the calibrator. The ELISA assay procedure is described herein.

The lyophilized secondary standard was assayed as an unknown sample in triplicate on a minimum of two assay plates per day for at least 10 days generating a minimum of 20 values (mean of triplicates). All values obtained for the secondary standard were averaged and the apo A-I value in milligrams per deciliter (mg/dl) was assigned.

Once the value assignment had been made, the secondary standard was used to construct a standard curve that was assayed on the same ELISA plate with a primary standard curve, with a complete set of controls. Primary and secondary standard curves were assayed on a minimum of 2 assay 96-well plates per day over a period of 5 days.

Once the value assignment of the secondary standard was accepted, standard curves were constructed and assayed on the same ELISA plate with the currently accepted lot of lyophilized standard over a period of five days (2 assay plates per day).

3. The Assay, Generally

Isolated AI-10 molecules were affixed to the walls of polystyrene microtiter plate wells (Nunc-Immuno Plate 1; Irving Scientific, Santa Ana, Calif.) by admixing 0.15 ml of a pH 9.0 sodium bicarbonate buffer containing 5 micrograms per milliliter ($\mu$g/ml) AI-10 into each well. The plates were maintained for 18 hours at 4 degrees C. and then washed 3 times with PBS containing 0.1 percent BSA and 0.05% polyoxyethyelene (20) sorbitan monolaurate (Tween 20). Residual, non-specific binding sites were then blocked by admixing 0.2 ml of PBS containing 10 percent BSA in each well, maintaining the admixture for 1 hour at 37 degrees C., followed by rinsing. Wells so prepared can be used for up to about one month after preparation when stored in a humdified chamber.

Human HDL was diluted in PBS to concentrations ranging from 1.0 to 0.031 $\mu$g/ml for use as standard control solutions. As noted before, human HDL rather than human apo A-I is used as a standard in these assays, because apo A-I has been found to be relatively unstable on storage whereas HDL appears to be relatively more storage-stable. Plasma (or serum) samples were diluted 1:5000 in PBS.

Fifty microliters ($\mu$l) of standard or sample were admixed in the wells in triplicate. Within about 5 minutes thereafter, 50 $\mu$l of PBS containing HRPO-labeled AI-11 paratopic molecules were admixed in each well. The immunoreaction admixtures were maintained for a time period of 30 minutes at 25 degrees C. Nonbound material was then separated from the wells by washing as described above.

The amount of solid phase-affixed sandwich immunoreactant containing HRPO label was then assayed by admixing 0.1 ml of freshly prepared substrate solution [distilled water containing 3 percent $H_2O_2$ and 0.67 mg/ml of o-phenylenediamine.

4. Step-wise Apo A-I HDL Sandwich ELISA

The following steps were carried out in performing the apolipoprotein A-I sandwich ELISA. Commercial controls were reconstituted according to package inserts with deionized water. The controls were swirled gently and maintained 20-30 minutes at room temperature to ensure complete solution.

a. Samples and Controls

Samples and controls are diluted 1:5000 in PBS. A serial dilution can be made as follows:

20 $\mu$l sample + 1.98 ml PBS (1:100);
40 $\mu$l of above dilution + 1.96 ml PBS (1:5000).

b. Standard Dilution

Isolated apo A-I (HDL) standard is diluted to 4 $\mu$g/ml in PBS. Then 2-fold serial dilutions to 0.031 $\mu$g/ml are made. For example, using a preparation of HDL designated 860527 that contained 868 $\mu$g/ml 4 $\mu$g/ml = 46 $\mu$l + 9.954 ml PBS (1:217);
2 $\mu$g/ml = 1 ml of above + 1 ml PBS; and
Continue 2-fold dilutions to 0.031 $\mu$g/ml.

c. HRPO-Labeled AI-11 Dilution

A 1:5000 dilution of AI-11 HRPO conjugate antibody in PBS is used. The following dilutions can be made:

20 $\mu$l + 1.98 ml PBS (1:100); and
240 $\mu$l of above + 11.76 ml PBS (1:5000).

Cover with foil to protect from light. This amount is sufficient for 2 plates.

d. 3 Percent Hydrogen Peroxide

Dilute 30 percent hydrogen peroxide ($H_2O_2$) 1:10 in distilled water.

e. o-Phenylenediamine Substrate

Dissolve 1 o-phenylenediamine (OPD) tablet (Sigma Chemical Co., St. Louis, Mo.) in 15 ml distilled water. Add 62.5 µl 3 percent $H_2O_2$. Cover with foil to protect from light. Make substrate fresh each time just before use.

5. Assay Procedure a. Equilibrate antibody-bound ELISA plate at ambient room temperature (20–22 degrees C.) for at least 20 minutes. Remove plate from bag and invert plate to remove residual buffer in wells. Fill the wells with 300 µl. Rinsing Buffer (PBS containing 0.1% BSA and 0.05% Tween 20, pH 7.2) and maintain for a time period of 10 minutes. Invert plate to remove buffer, and blot plate dry on paper toweling. Do not allow wells to sit empty longer than 10 minutes during the assay.

b. Add 50 µl standard or sample to wells in triplicate. The 0 µg/ml standard is 50 µl of PBS.

Add 50 µl diluted HDL standards to the standard wells (0.031, 0.062, 0.125, 0.25, 0.50, 1.0 µg/ml).

Add 50 µl of diluted controls and patient samples to their respective wells.

c. Add 50 µl/well of HRPO-linked antibody to all wells.

d. Wrap plate in aluminum foil and place on a gyroshaker (about 100 RPM) for 30 minutes at ambient room temperature (about 20–25 degrees C.).

e. Wash the plate by filling the wells with 300 µl/well of Rinsing Buffer and then inverting the plate to remove the buffer. Repeat two more times for a total of three washes. Blot plate dry on paper toweling after third wash. Do not allow the plate to dry out.

f. Add 100 µl/well of freshly-prepared OPD substrate. Allow color to develop at room temperature for 30 minutes.

g. Stop reaction with 50 µl of 4N Sulfuric Acid to all wells. Read O.D. at 492 nm.

I. Plasma Samples and

Lipoprotein Quantification

Plasma samples were obtained from 20 patients with coronary artery disease from the cardiac catheterization laboratory at the San Diego VA Hospital. In addition, plasma was obtained from 37 normal subjects.

Blood was collected into tubes containing 1.5 mg/ml ethylenediamine tetraacetate (EDTA), and the plasma was separated immediately by centrifugation at 4 degrees C.

Total plasma cholesterol and triglycerides were measured on fresh plasma samples in a standardized clinical laboratory using an Abbott ABA-200 bichromatic analyzer, and Boehringer-Mannheim high performance cholesterol reatent 236691 and Abbott Laboratories triglycerides A-gent. LDL- and HDL-cholesterol were measured using techniques described in *Lipid Research Clinic Procedures*, HEW Pub. No. 75-628 (NIH), 2 ed., Washington, D.C., Gov. Print. Off., (1974).

Quantitative apolipoprotein A-I assays were also carried out using commercially available assay kits supplied by Isotex Diagnostics of Friendswood, Tex.; Ventrex Laboratories, Inc. of Portland, Me.; Tago, Inc. of Burlingame, Calif.; and Calbiochem-Behring of La Jolla, Calif. Instructions supplied with each kit were followed in carrying out the assays.

Quantitative ELISA studies for apo A-I were carried out as described herein on serum or plasma samples obtained from donors, as already described, or on samples obtained from laboratory preparations, as gifts or from commercial suppliers. Those commercial samples were obtained from: Meloy Laboratories of Springfield, Va.; Scripps Laboratories of La Jolla, Calif.; Omega/Cooper Biomedical Inc. of Malvern, Pa.; Isolab Lab of Akron, OH; Calbiochem-Behring of La Jolla, Calif.; International Union of Immunological Standards (IUIS) available through the Centers for Disease Control, Atlanta, Ga.; and Chemicon International, Inc. of El Segundo, Calif. Gift samples were kindly provided by Ortho Diagnostic Systems, Inc. of Raritan, N.J. Apo A-I standards were obtained from Meloy Laboratories, Scripps Laboratories and Chemicon International.

J. Fluid Phase $^{125}$I-Labeled Antigen RIA

To determine the fraction of $^{125}$I-HDL particles and apo A-I bound by AI-10, AI-11, AI-12, AI-13 and AI-14, a fluid phase RIA was utilized [Curtiss and Edgington (1985) *J. Biol. Chem.* 260:2982–2993]. Thus, to 0.1 ml of radioiodinated antigen (HDL or apolipoprotein A-I) were added 0.1 ml of phosphate-buffered saline, pH 7.2, and 0.1 ml of varying dilutions of mouse hybridoma culture fluid or ascites fluid diluted in 1:50 normal mouse serum. All buffers also contained 5% dextran (m.w. 40,000). After 18 hours at 4 degrees C., 0.1 ml of precipitating second antibody (goat anti-mouse IgG serum) was added. Following a 4-hour incubation at 4 degrees C., 2 ml of cold PBS were added, and the tubes were centrifuged at 2000xg for 30 minutes at 4 degrees C. Supernatants were decanted and the 125I activity of the pellets determined in a gamma counter.

Maximum precipitable radioactivity was determined by replacing the second antibody with 100% TCA. The minimum precipitable radioactivity or non-specific binding (NSB) was determined by replacing the specific hybridoma antibodies with an irrelevant hybridoma antibody of the same heavy chain class.

Data were calculated as:

$$\text{percent of } ^{125}I\text{-antigen bound} = \frac{\text{MEAN} - \text{NSB} \times 100}{\text{TCA} - \text{NSB}}$$

where "MEAN" is the mean radioactivity precipitated in the presence of a given amount of specific antibody, "NSB" is the amount of non-specifically bound radioactivity precipitated that was determined by replacing the specific paratopic molecules of the invention with an irrelevant hybridoma antibody of the same heavy chain class, and "TCA" is the maximum TCA-precipitable radioactivity.

K. Competitive Immunoenzymometric Assay for AI-10 and AI-11

Flexible polyvinyl chloride microtiter plates were coated for a time period of about 18 hours (overnight) at 4 degrees C with 0.2 ml of phosphate-buffered saline (PBS) containing 5 µg/ml of either HDL or purified apo A-I. The wells were washed three times with 0.3 ml of PBS containing 1.0 g BSA and 0.5 ml Tween 20 per liter. Residual binding sites on the wells were blocked by incubating 0.2 ml of PBS containing 30 BSA per liter in the wells for 1 hour at ambient temperature (20–25 degrees C.). The wells were then washed three times with rinsing buffer. Plates were used immediately.

PBS (0.05 ml) containing 0.375 µg/ml of AI-10 conjugated with horseradish peroxidase was incubated in the pre-coated wells with 0.05 ml of PBS containing from 0 to 8.0 µg/ml of unconjugated AI-10 or unconjugated AI-11 monoclonal antibody. Incubation time was three hours at ambient temperature. Wells were then washed three times with rinsing buffer and 0.1 ml of PBS containing o-phenylenediamine substrate was added to all the wells, and incubated for 30 minutes at ambient temperature (20-25 degrees C.). The color reaction was stopped by the addition of 0.05 ml of 4N $H_2SO_4$ to all wells, and the optical density (O.D.) of each well was determined at 490 nanometers (nm) using a Dynatech 96-well plate reader.

Results of the apo A-I coated plate are shown in FIG. 1 and results of the HDL coated plate are shown in FIG. 2. A 21-fold increase of unlabeled AI-II molecules did not significantly compete with peroxidase-labeled AI-10 molecules for binding to HDL or apo A-I. The study has been repeated using peroxidase-labeled AI-11 with unlabeled AI-10 and AI-11 at the same concentrations with substantially the same results.

The present invention has been described with respect to preferred embodiments. It will be clear to those skilled in the art that modifications and/or variations of the disclosed subject matter can be made without departing from the scope of the invention set forth herein.

What is claimed is:

1. A monoclonal paratopic molecule that immunologically reacts with apolipoprotein A-I and is secreted by a hybridoma selected from the group consisting of those hybridomas having the ATCC accession numbers HB 9200, HB 9201, HB 9202, HB 9203, and HB 9204.

2. The monoclonal paratopic molecule of claim 1 that is a whole antibody

3. A method for assaying for the presence of apolipoprotein A-I in a liquid sample comprising the steps of:
(a) admixing a liquid sample to be assayed with an effective amount of monoclonal paratopic molecules that immunoreact with apolipoprotein A-I and are secreted by a hybridoma selected from the group consisting of those hybridomas having the ATCC accession numbers HB 9200, HB 9201, HB 9202, HB 9203, and HB 9204 to form an admixture;
(b) maintaining said admixture under biological assay conditions for a predetermined period of time sufficient for said paratopic molecules to immunoreact with apolipoprotein A-I present in the sample and form an immunoreactant;
(c) determining the presence of an immunoreactant.

4. The method of claim 3 wherein said paratopic molecules contain an operatively-linked radioactive element, and the presence of said apolipoprotein A-I is determined by separating the immunoreactant from the remainder of the admixture and assaying the emitted radiation of the separated immunoreactant.

5. The method of claim 4 wherein said separation is carried out by admixture of said first-named admixture with antibodies that immunoreact with said paratopic molecules to form a second admixture, maintenance of the second admixture under biological assay conditions for a predetermined time period sufficient for a further immunoreactant to form, and centrifugally separating said further immunoreactant from the remainder of said second admixture.

6. The method of claim 3 wherein said first-named monoclonal paratopic molecules are bound to a solid matrix to form a solid support prior to said admixture, the non-specific protein binding sites of said solid support are blocked, and said immunoreactant formed is bound to said solid support as a solid phase-bound immunoreactant.

7. The method of claim 6 wherein the presence of said solid phase-bound immunoreactant is determined by:
(i) admixing liquid phase second monoclonal paratopic molecules with said first-named admixture to form a second admixture, said second paratopic molecules immunoreacting with apolipoprotein A-I and being secreted by a hybridoma selected from the group consisting of those hybridomas having the ATCC accession numbers HB 9200, HB 9201, HB 9202, HB 9203, and HB 9204 but are not utilized in said first-named admixture, said second paratopic molecules being operatively linked to an enzyme indicating means;
(ii) maintaining said second admixture under biological assay conditions for a predetermined period of time sufficient for said second indicating means-linked paratopic molecules to immunoreact with apolipoprotein A-I present in said admixture and form a sandwich immunoreactant and a liquid phase;
(iii) separating the solid and liquid phases; and
(iv) determining the presence of indicating means-linked apolipoprotein A-I in the separated solid phase sandwich immunoreactant, and thereby the presence of apolipoprotein A-I in said sample.

8. The method of claim 7 wherein said first-named paratopic molecules of the solid support and said second indicating means-linked paratopic molecules are admixed substantially simultaneously with said sample, and said maintaining steps are carried out together.

9. A method of determining the amount of apolipoprotein A-I present in a liquid sample comprising the steps of:
(a) admixing a predetermined amount of liquid sample with a solid support consisting essentially of a solid matrix having solid phase-bound first monoclonal paratopic molecules that immunoreact with apolipoprotein A-I and are secreted by one of the hybridomas having ATCC accession numbers HB 9200 or HB 9201 to form a solid-liquid phase admixture, the surface of said support having blocked non-specific protein binding sites;
(b) maintaining said solid-liquid phase admixture under biological assay conditions for a predetermined period of time sufficient for said first paratopic molecules to immunoreact with apolipoprotein A-I present in the sample and form a solid phase-bound immunoreactant that contains substantially all of the apolipoprotein A-I present in the sample;
(c) admixing apolipoprotein A-I in said liquid sample with liquid phase second monoclonal paratopic molecules that immunoreact with apolipoprotein A-I, are secreted by one of the hybridomas having ATCC accession numbers HB 9200 or HB 9201 but are not utilized in said first-named admixture, and are operatively linked to an enzyme indicating means to form a second admixture;
(d) maintaining said second admixture under biological assay conditions for a predetermined period of time sufficient for said second indicating means-linked paratopic molecules to form an immunoreactant that contains substantially all apolipoprotein B-100 in the sample;
(e) separating the solid and liquid phases that result from above steps (a–d); and
(f) determining the amount of indicating means-linked apolipoprotein A-I-containing immunoreactant present in the separated solid phase, and thereby the amount of apolipoprotein A-I in said sample.

10. The method of claim 9 wherein said admixing steps (a) and (c) are carried out substantially simultaneously, and said maintaining steps (b) and (d) are carried out together.

11. The method of claim 9 wherein the solid and liquid phases present after step (b) are separated prior to step (c), and the apolipoprotein A-I in said sample is present in the solid phase-bound immunoreactant formed in step (b).

12. The method of claim 9 wherein said liquid sample is a blood sample.

13. A method of determining the amount of apolipoprotein A-I present in a liquid blood sample comprising the steps of:
 (a) forming a solid-liquid phase admixture by substantially simultaneously admixing a liquid blood sample with a solid support consisting essentially of a solid matrix having solid phase-bound first monoclonal paratopic molecules that immunoreact with apolipoprotein A-I and are secreted by one of hybridomas having ATCC accession numbers HB 9200 or HB 9201, and second liquid phase monoclonal paratopic molecules operatively linked to an enzyme indicating means that are secreted by either of hybridomas having ATCC accession numbers HB 9200 or HB 9201 and are not the first paratopic molecules bound to the solid matrix, the surface of said support having blocked, non-specific protein binding sites;
 (b) maintaining said solid-liquid phase admixture under biological assay conditions for a predetermined period of time sufficient for said first paratopic molecules and said indicating means-linked second paratopic molecules to immunoreact with substantially all apolipoprotein A-I present in the sample to form a solid phase-bound sandwich immunoreactant and a liquid phase;
 (c) separating the solid and liquid phases; and
 (d) determining the amount of indicating means-linked apolipoprotein A-I-containing sandwich immunoreactant present in the separated solid phase, and thereby the amount of apolipoprotein A-I in said sample.

14. The method of claim 13 wherein said first paratopic molecules are secreted by the hybridoma having ATCC accession number HB 9200.

15. The method of claim 13 wherein said maintenance under biological assay conditions is for a time period of about 30 minutes to about 60 minutes at ambient room temperature.

16. A diagnostic system suitable for use in determining the presence of apolipoprotein A-I in a liquid sample comprising:
 a) a package having paratopic molecules that immunoreact with apolipoprotein A-I and are secreted by one of the hybridomas selected from the group consisting of those hybridomas having ATCC accession numbers HB 9200, HB 9201, HB 9202, HB 9203, and HB 9204;
 said paratopic molecules being present in an amount sufficient to carry out one determination of the presence of apolipoprotein A-I.

17. The diagnostic system of claim 16 further including an indicating means.

18. The diagnostic system of claim 17 wherein said indicating means is operatively linked to molecules that react with said paratopic molecules.

19. A diagnostic system suitable for use in determining the amount of apolipoprotein A-I present in a liquid blood sample comprising:
 (a) a first package containing a solid support consisting essentially of a solid matrix having monoclonal paratopic molecules that immunoreact with apolipoprotein A-I and are secreted by one of the hybridomas having ATCC accession numbers HB 9200 or HB 9201 bound to said matrix, the non-specific protein binding sites of said support being blocked; and
 (b) a second package containing monoclonal paratopic molecules that immunoreact with apolipoprotein A-I, are secreted by one of the hybridomas having ATCC accession numbers HB 9200 or HB 9201 but are not the paratopic molecules of said first package, and are operatively linked to an enzyme indicating means;
 said paratopic molecules being present in an amount sufficient to carry out one determination of the presence of apolipoprotein A-I.

20. The diagnostic system of claim 19 wherein monoclonal paratopic molecules secreted by the hybridoma having ATCC accession number HB 9200 are bound to said solid matrix of said first package.

21. A hybridoma having the ATCC accession number HB 9200.

22. A hybridoma having the ATCC accession number HB 9201.

23. A hybridoma having the ATCC accession number HB 9202.

24. A hybridoma having the ATCC accession number HB 9203.

25. A hybridoma having the ATCC accession number HB 9204.

* * * * *

UNITED STATES PATENT AND TRADEMARK OFFICE
CERTIFICATE OF CORRECTION

PATENT NO. : 5,126,240
DATED : June 30, 1992
INVENTOR(S) : Curtiss

It is certified that error appears in the above-identified patent and that said Letters Patent is hereby corrected as shown below:

In Column 1, line 4, insert:

-- This invention was made with government support under Grant No. HL 14197 awarded by the National Institutes of Health. The government has certain rights in the invention. --

Signed and Sealed this

Fifteenth Day of February, 1994

Attest:

BRUCE LEHMAN

Attesting Officer

Commissioner of Patents and Trademarks